(12) United States Patent
Arkenau et al.

(10) Patent No.: US 8,114,384 B2
(45) Date of Patent: *Feb. 14, 2012

(54) PROCESS FOR THE PRODUCTION OF AN ABUSE-PROOFED SOLID DOSAGE FORM

(75) Inventors: Elisabeth Arkenau, Aachen (DE); Johannes Bartholomäus, Aachen (DE)

(73) Assignee: Gruenenthal GmbH, Aachen (DE)

(*) Notice: Subject to any disclaimer, the term of this patent is extended or adjusted under 35 U.S.C. 154(b) by 377 days.

This patent is subject to a terminal disclaimer.

(21) Appl. No.: 10/890,704

(22) Filed: Jul. 14, 2004

(65) Prior Publication Data

US 2006/0002859 A1    Jan. 5, 2006

(30) Foreign Application Priority Data

Jul. 1, 2004 (DE) .......................... 10 2004 032 051

(51) Int. Cl.
*A61K 49/00* (2006.01)

(52) U.S. Cl. ..................................... 424/10.1; 424/10.4

(58) Field of Classification Search .................. 424/10.1
See application file for complete search history.

(56) References Cited

U.S. PATENT DOCUMENTS

| | | |
|---|---|---|
| 3,806,603 A | 4/1974 | Gaunt et al. |
| 3,865,108 A | 2/1975 | Hartop |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,207,893 A | 6/1980 | Michaels |
| 4,262,017 A | 4/1981 | Kuipers |
| 4,343,789 A | 8/1982 | Kawata et al. |
| 4,353,887 A | 10/1982 | Hess |
| 4,404,183 A | 9/1983 | Kawata et al. |
| 4,427,681 A | 1/1984 | Manshi |
| 4,462,941 A | 7/1984 | Lee et al. |
| 4,603,143 A | 7/1986 | Schmidt |
| 4,612,008 A | 9/1986 | Wong et al. |
| 4,629,621 A | 12/1986 | Snipes |
| 4,690,822 A | 9/1987 | Uemura et al. |
| 4,713,243 A | 12/1987 | Schiraldi et al. |
| 4,744,976 A | 5/1988 | Snipes et al. |
| 4,764,378 A | 8/1988 | Kein et al. |
| 4,765,989 A | 8/1988 | Wong et al. |
| 4,774,074 A | 9/1988 | Snipes |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,957,668 A | 9/1990 | Placard |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinity et al. |
| 5,169,645 A | 12/1992 | Shukla et al. |
| 5,198,226 A | 3/1993 | MacFarlane et al. |
| 5,200,197 A | 4/1993 | Wright et al. |
| 5,211,892 A | 5/1993 | Gueret |
| 5,273,758 A | 12/1993 | Royce |
| 5,350,741 A | 9/1994 | Takada |
| 5,378,462 A | 1/1995 | Boedecker et al. |
| 5,427,798 A | 6/1995 | Ludgwig et al. |
| RE34,990 E | 7/1995 | Khanna et al. |
| 5,458,887 A | 10/1995 | Chen et al. |
| 5,460,826 A | 10/1995 | Merrill et al. |
| 5,556,640 A | 9/1996 | Ito et al. |
| 5,562,920 A | 10/1996 | Demmer et al. |
| 5,601,842 A | 2/1997 | Bartholomaeus |
| 5,620,697 A | 4/1997 | Tormala et al. |
| 5,681,517 A | 10/1997 | Metzger |
| 5,792,474 A | 8/1998 | Rauchfuss |
| 5,801,201 A | 9/1998 | Gradums et al. |
| 5,811,126 A | 9/1998 | Krishnamurthy |
| 5,849,240 A | 12/1998 | Miller et al. |
| 5,866,164 A | 2/1999 | Kuczynski et al. |
| 5,916,584 A | 6/1999 | O'Donoghue et al. |
| 5,928,739 A | 7/1999 | Pophusen et al. |

(Continued)

FOREIGN PATENT DOCUMENTS

AR    46994    12/2004

(Continued)

OTHER PUBLICATIONS

Maggi et al. (Biomaterials 2002, 23, 1113-1119).*
Zhang et al. (Pharm. Dev. Tech. 1999, 4, 241-250).*
DeJong (Pharmaceutisch Weekblad Scientific Edition 1987, p. 24-28).*
"Coated Pharmaceutical Dosage Forms, Fundamentals, Manufacturing Techniques, Biopharmaceutical Aspects, Test Methods and Raw Materials", Kurt H. Bauer, Ph. D., et al., 1998, table of contents.
Schroeder R. et. al, "Granulierung Hydrophober Wirkstoffe Im Planetwalzenenxtruder Granulation of Hydrophobic Actives with the Planetary Roller Extruder," Pharmazeutische Industrie, Aulendorf, DE, vol. 65, No. 4, 2003, pp. 367-372.
Proeschel et al, "Task-dependence of activity / bite-force relations and its impact on estimation of chewing force from EMG"; J. Dent Res, 81 (7); pp. 464-468 (2002).
Observations by Third Parties Pursuant to Art 115 EPC, dated Feb. 2, 2009.
Letter of James W. McGinity, with attached experimental report, dated Jan. 26, 2009.
El-Egakey, Adel et al, Pharmacerutica Acta Helvetiae, vol. 46, Mar. 19, 1970.
Apicella A., Biomaterials, vol. 14, No. 2, pp. 83-90, 1993.

(Continued)

*Primary Examiner* — Michael G Hartley
*Assistant Examiner* — Melissa Perreira
(74) *Attorney, Agent, or Firm* — Norris McLaughlin & Marcus, P.A.

(57) ABSTRACT

The present invention relates to a process for the production of an abuse-proofed solid dosage form containing at least one active ingredient with potential for abuse and a synthetic or natural polymer with a breaking strength of =500 N, characterized in that a corresponding mixture is processed by melt extrusion with the assistance of a planetary-gear extruder.

14 Claims, 2 Drawing Sheets

U.S. PATENT DOCUMENTS

| | | | |
|---|---|---|---|
| 5,945,125 | A | 8/1999 | Kim |
| 5,948,787 | A | 9/1999 | Merrill et al. ................. 514/282 |
| 5,968,925 | A | 10/1999 | Knidlberger |
| 6,009,390 | A | 12/1999 | Gupta et al. |
| 6,009,690 | A * | 1/2000 | Rosenberg et al. ............. 53/454 |
| 6,077,538 | A | 6/2000 | Merrill et al. |
| 6,096,339 | A | 8/2000 | Ayer et al. |
| 6,117,453 | A | 9/2000 | Seth et al. |
| 6,133,241 | A | 10/2000 | Bok et al. |
| 6,228,863 | B1 | 5/2001 | Palermo et al. |
| 6,235,825 | B1 | 5/2001 | Yoshida et al. |
| 6,238,697 | B1 * | 5/2001 | Kumar et al. ................. 424/464 |
| 6,245,357 | B1 | 6/2001 | Edgren et al. |
| 6,248,737 | B1 * | 6/2001 | Buschmann et al. ...... 514/231.8 |
| 6,261,599 | B1 | 7/2001 | Oshlack |
| 6,306,438 | B1 | 10/2001 | Oshlack et al. |
| 6,309,668 | B1 | 10/2001 | Bastin et al. |
| 6,340,475 | B2 | 1/2002 | Shell et al. |
| 6,344,535 | B1 | 2/2002 | Timmermann et al. |
| 6,348,469 | B1 | 2/2002 | Seth |
| 6,375,963 | B1 | 4/2002 | Repka et al. |
| 6,399,100 | B1 | 6/2002 | Clancy et al. |
| 6,419,954 | B1 | 7/2002 | Chu et al. |
| 6,436,441 | B1 | 8/2002 | Sako et al. |
| 6,461,644 | B1 | 10/2002 | Jackson et al. |
| 6,488,962 | B1 | 12/2002 | Berner et al. |
| 6,488,963 | B1 | 12/2002 | McGinity et al. |
| 6,534,089 | B1 | 3/2003 | Ayer et al. |
| 6,547,997 | B1 | 4/2003 | Breithenbach et al. |
| 6,562,375 | B1 | 5/2003 | Sako |
| 6,592,901 | B2 | 7/2003 | Durig et al. |
| 6,635,280 | B2 | 10/2003 | Shell et al. |
| 6,699,503 | B1 | 3/2004 | Sako et al. |
| 6,723,340 | B2 | 4/2004 | Gusler et al. |
| 6,733,783 | B2 * | 5/2004 | Oshlack et al. ............... 424/473 |
| 6,753,009 | B2 | 6/2004 | Luber |
| 6,821,588 | B1 | 11/2004 | Hammer |
| 7,141,250 | B2 | 11/2006 | Oshlack et al. |
| 7,176,251 | B1 | 2/2007 | Bastioli et al. |
| 7,776,314 | B2 | 8/2010 | Bartholomäus et al. |
| 2001/0038852 | A1 | 11/2001 | Kolter et al. |
| 2002/0001270 | A1 | 1/2002 | Fukuchi et al. |
| 2002/0015730 | A1 | 2/2002 | Hoffmann et al. |
| 2002/0018719 | A1 | 2/2002 | Arilla et al. |
| 2002/0051820 | A1 | 5/2002 | Shell et al. |
| 2002/0114838 | A1 | 8/2002 | Ayer et al. |
| 2002/0132359 | A1 | 9/2002 | Waterman |
| 2003/0015814 | A1 | 1/2003 | Krull et al. |
| 2003/0017532 | A1 | 1/2003 | Biswas et al. |
| 2003/0021546 | A1 | 1/2003 | Sato |
| 2003/0031546 | A1 | 2/2003 | Araki et al. |
| 2003/0044458 | A1 | 3/2003 | Wright et al. |
| 2003/0044464 | A1 | 3/2003 | Ziegler et al. |
| 2003/0064099 | A1 * | 4/2003 | Oshlack et al. ................. 424/465 |
| 2003/0068392 | A1 | 4/2003 | Sackler ......................... 424/760 |
| 2003/0091630 | A1 | 5/2003 | Louie-Helm et al. |
| 2003/0104052 | A1 | 6/2003 | Berner et al. |
| 2003/0118641 | A1 | 6/2003 | Maloney et al. |
| 2003/0124185 | A1 | 7/2003 | Oshlack et al. ............... 424/465 |
| 2003/0125347 | A1 | 7/2003 | Anderson |
| 2003/0133985 | A1 | 7/2003 | Louie-Helm et al. |
| 2003/0152622 | A1 | 8/2003 | Louie-Helm et al. |
| 2003/0158242 | A1 | 8/2003 | Kugelmann |
| 2003/0175326 | A1 | 9/2003 | Thombre |
| 2003/0232895 | A1 | 12/2003 | Omidian et al. |
| 2004/0010000 | A1 | 1/2004 | Ayer et al. |
| 2004/0011806 | A1 | 1/2004 | Luciano et al. |
| 2004/0052844 | A1 | 3/2004 | Hsiao et al. |
| 2004/0081694 | A1 | 4/2004 | Oshlack |
| 2004/0091528 | A1 | 5/2004 | Rogers et al. |
| 2004/0131671 | A1 | 7/2004 | Zhang et al. |
| 2004/0156899 | A1 | 8/2004 | Louie-Helm et al. |
| 2004/0170567 | A1 | 9/2004 | Sackler |
| 2004/0185105 | A1 | 9/2004 | Berner et al. |
| 2004/0213848 | A1 | 10/2004 | Li et al. |
| 2005/0015730 | A1 | 1/2005 | Gunturi et al. |
| 2005/0031546 | A1 | 2/2005 | Bartholomaus et al. |
| 2005/0058706 | A1 | 3/2005 | Bartholomaeus et al. |
| 2005/0063214 | A1 | 3/2005 | Takashima |
| 2005/0089475 | A1 | 4/2005 | Gruber |
| 2005/0095291 | A1 | 5/2005 | Oshlack et al. |
| 2005/0106249 | A1 | 5/2005 | Hwang et al. |
| 2005/0112067 | A1 | 5/2005 | Kumar et al. |
| 2005/0127555 | A1 * | 6/2005 | Gusik et al. .................... 264/143 |
| 2005/0152843 | A1 | 7/2005 | Bartholomaeus et al. |
| 2005/0186139 | A1 | 8/2005 | Bartholomaeus et al. |
| 2005/0191244 | A1 | 9/2005 | Bartholomaus |
| 2005/0214223 | A1 | 9/2005 | Bartholomaeus et al. |
| 2005/0236741 | A1 | 10/2005 | Arkenau et al. |
| 2005/0266084 | A1 | 12/2005 | Li et al. |
| 2006/0002859 | A1 | 1/2006 | Arkenau et al. |
| 2006/0002860 | A1 | 1/2006 | Bartholomaeus et al. |
| 2006/0039864 | A1 | 2/2006 | Bartholomaeus et al. |
| 2006/0099250 | A1 | 5/2006 | Tian et al. |
| 2006/0188447 | A1 | 8/2006 | Arkenau-Maric et al. |
| 2006/0193782 | A1 | 8/2006 | Bartholomaeus et al. |
| 2006/0193914 | A1 | 8/2006 | Ashworth et al. |
| 2006/0240110 | A1 | 10/2006 | Kiick et al. |
| 2007/0003616 | A1 | 1/2007 | Arkenau-Maric et al. |
| 2007/0020188 | A1 | 1/2007 | Sackler |
| 2007/0020335 | A1 | 1/2007 | Chen et al. |
| 2007/0048228 | A1 | 3/2007 | Arkenau-Maric et al. |
| 2007/0065365 | A1 | 3/2007 | Kugelmann et al. |
| 2007/0092573 | A1 | 4/2007 | Joshi et al. |
| 2007/0183979 | A1 | 8/2007 | Arkenau-Maric et al. |
| 2007/0183980 | A1 | 8/2007 | Arkenau-Maric et al. |
| 2007/0190142 | A1 | 8/2007 | Breitenbach et al. |
| 2007/0196396 | A1 | 8/2007 | Pilgaonkar et al. |
| 2007/0196481 | A1 | 8/2007 | Amidon et al. |
| 2007/0264327 | A1 | 11/2007 | Kumar et al. |
| 2007/0269505 | A1 | 11/2007 | Flath |
| 2008/0081290 | A1 | 4/2008 | Wada et al. |
| 2008/0247959 | A1 | 10/2008 | Bartholomaus et al. |
| 2008/0248113 | A1 | 10/2008 | Bartholomaus et al. |
| 2008/0311049 | A1 | 12/2008 | Bartholomaus et al. |
| 2008/0311187 | A1 | 12/2008 | Ashworth et al. |
| 2008/0311197 | A1 | 12/2008 | Arkenau-Maric et al. |
| 2008/0312264 | A1 | 12/2008 | Arkenau-Maric et al. |
| 2008/0317854 | A1 | 12/2008 | Arkenau et al. |
| 2009/0004267 | A1 | 1/2009 | Arkenau-Maric et al. |
| 2009/0005408 | A1 | 1/2009 | Arkenau-Maric et al. |
| 2009/0081290 | A1 | 3/2009 | Kckenna et al. |
| 2009/0202634 | A1 | 8/2009 | Jozef et al. |
| 2010/0015223 | A1 | 1/2010 | Cailly-Dufestel et al. |
| 2010/0098758 | A1 | 4/2010 | Bartholomaus et al. |
| 2010/0151028 | A1 | 6/2010 | Ashworth et al. |
| 2010/0221322 | A1 | 9/2010 | Bartholomaus et al. |
| 2010/0260833 | A1 | 10/2010 | Bartholomaus et al. |
| 2011/0020451 | A1 | 1/2011 | Bartholomaus et al. |
| 2011/0038930 | A1 | 2/2011 | Barnscheid et al. |
| 2011/0082214 | A1 | 4/2011 | Fauer et al. |

FOREIGN PATENT DOCUMENTS

| | | |
|---|---|---|
| AR | 045353 | 10/2005 |
| AR | 049562 | 8/2006 |
| AR | 053304 | 5/2007 |
| AR | 054222 | 6/2007 |
| AR | 054328 | 6/2007 |
| AU | 2003237994 | 12/2003 |
| AU | 2003274071 | 5/2004 |
| AU | 2003278133 | 5/2004 |
| AU | 2003279317 | 5/2004 |
| AU | 2004264666 | 2/2005 |
| AU | 2004264667 | 2/2005 |
| AU | 2004308653 | 4/2005 |
| AU | 2005259476 | 1/2006 |
| AU | 2005259478 | 1/2006 |
| AU | 2006210145 | 8/2006 |
| AU | 2009207796 | 7/2009 |
| AU | 2009243681 | 11/2009 |
| BR | P10413318 | 10/2006 |
| BR | P10413361 | 10/2006 |
| BR | P10513300 | 5/2008 |
| BR | P10606145 | 2/2009 |
| CA | 2317747 | 7/1999 |
| CA | 2352874 A1 * | 11/1999 |
| CA | 2502965 | 5/2004 |

| | | | | | |
|---|---|---|---|---|---|
| CA | 2534925 | 2/2005 | EP | 0696598 | 2/1996 |
| CA | 2534932 | 2/2005 | EP | 0756480 | 2/1997 |
| CA | 2551231 | 7/2005 | EP | 0 761 211 A1 | 3/1997 |
| CA | 2572352 | 1/2006 | EP | 0760654 | 3/1997 |
| CA | 2572491 | 1/2006 | EP | 0780369 A1 | 6/1997 |
| CA | 2595954 | 7/2006 | EP | 0785775 | 7/1997 |
| CA | 2595979 | 8/2006 | EP | 0809488 | 12/1997 |
| CA | 2713128 | 7/2009 | EP | 0820698 A1 | 1/1998 |
| CA | 2723438 | 11/2009 | EP | 0857062 | 8/1998 |
| CH | 689109 | 10/1998 | EP | 0864324 | 9/1998 |
| CN | 1980643 | 4/2005 | EP | 0864326 | 9/1998 |
| CN | 101010071 | 6/2005 | EP | 0 980 894 A1 | 3/1999 |
| CN | 101022787 | 1/2006 | EP | 0988106 | 3/2000 |
| CN | 001863513 | 11/2006 | EP | 1014941 | 7/2000 |
| CN | 001863514 | 11/2006 | EP | 1070504 | 1/2001 |
| CN | 01917862 | 2/2007 | EP | 1127871 | 8/2001 |
| CN | 101027044 | 8/2007 | EP | 1138321 | 10/2001 |
| CN | 101111232 | 1/2008 | EP | 1166776 | 1/2002 |
| CN | 101175482 | 2/2008 | EP | 1250045 | 10/2002 |
| DE | 2530563 | 1/1977 | EP | 1251120 | 10/2002 |
| DE | 2530563 A1 | 1/1977 | EP | 1293127 | 3/2003 |
| DE | 4309528 A1 | 9/1994 | EP | 1293196 | 3/2003 |
| DE | 69400215 T2 | 10/1996 | EP | 1658055 | 2/2005 |
| DE | 19522899 C1 | 12/1996 | EP | 1515702 | 3/2005 |
| DE | 2808505 | 1/1997 | EP | 1527775 | 4/2005 |
| DE | 19753534 A1 | 6/1999 | EP | 1558221 A1 | 8/2005 |
| DE | 19800689 | 7/1999 | EP | 1558257 | 8/2005 |
| DE | 19800698 A1 | 7/1999 | EP | 1560585 | 8/2005 |
| DE | 19822979 A1 | 12/1999 | EP | 1658054 | 5/2006 |
| DE | 69229881 | 12/1999 | EP | 1740161 | 1/2007 |
| DE | 19855440 | 6/2000 | EP | 1765303 | 3/2007 |
| DE | 19856147 | 6/2000 | EP | 1786403 | 5/2007 |
| DE | 19940740 | 3/2001 | EP | 1558221 B1 | 6/2007 |
| DE | 19960494 | 6/2001 | EP | 1845955 | 10/2007 |
| DE | 10036400 | 6/2002 | EP | 1845956 | 10/2007 |
| DE | 69429710 T2 | 8/2002 | EP | 1859789 | 11/2007 |
| DE | 10250083 A1 | 12/2003 | EP | 1897545 | 12/2008 |
| DE | 10250084 | 5/2004 | EP | 2131830 | 12/2009 |
| DE | 10250087 | 5/2004 | EP | 2249811 | 11/2010 |
| DE | 10250088 | 5/2004 | EP | 2273983 | 1/2011 |
| DE | 10336400 | 3/2005 | ES | 2336571 | 12/2004 |
| DE | 102004019916 | 11/2005 | ES | 2260042 | 11/2006 |
| DE | 102004020220 | 11/2005 | ES | 2285497 | 11/2007 |
| DE | 10 2004 032049 | 1/2006 | ES | 2288621 | 1/2008 |
| DE | 10 2004 032051 | 1/2006 | ES | 2289542 | 2/2008 |
| DE | 10 2004 032 103 | 1/2006 | ES | 2315505 | 4/2009 |
| DE | 10 2005 005446 | 8/2006 | GB | 1147210 A | 4/1969 |
| DE | 10 2005 005449 | 8/2006 | GB | 2057878 | 4/1981 |
| DE | 102007011485 | 9/2008 | HR | P20070272 | 6/2007 |
| DK | 1658055 | 7/2007 | HR | 20070456 | 11/2007 |
| DK | 1658054 | 10/2007 | JP | 8 505076 | 6/1996 |
| DK | 1515702 | 1/2009 | JP | 2002-275175 | 9/2002 |
| EC | SP066345 | 8/2006 | JP | 2005534664 | 11/2005 |
| EP | 0008131 | 2/1980 | KR | 1020060069832 | 6/2006 |
| EP | 0216453 | 2/1980 | KR | 20070039041 | 4/2007 |
| EP | 0043254 A1 | 1/1982 | KR | 20070111510 | 11/2007 |
| EP | 0177893 | 4/1986 | KR | 20100111303 | 10/2010 |
| EP | 0226061 | 6/1987 | KR | 20110016921 | 2/2011 |
| EP | 0228417 | 7/1987 | MX | 2007000008 | 3/2007 |
| EP | 0229652 A2 | 7/1987 | MX | 2007000009 | 3/2007 |
| EP | 0232877 | 8/1987 | MX | 2007009393 | 8/2007 |
| EP | 02 40906 | 10/1987 | MX | 2010008138 | 8/2010 |
| EP | 0261616 A2 | 3/1988 | MX | 2010012039 | 11/2010 |
| EP | 0270954 | 6/1988 | NO | 20061054 | 3/2006 |
| EP | 0277289 | 8/1988 | NO | 20070578 | 1/2007 |
| EP | 0293066 | 11/1988 | NO | 20074412 | 11/2007 |
| EP | 0328775 | 8/1989 | PT | 1699440 | 12/2004 |
| EP | 0477135 A1 | 3/1992 | PT | 1658054 | 5/2006 |
| EP | 0544144 | 6/1993 | PT | 1658055 | 7/2007 |
| EP | 0583726 | 2/1994 | PT | 1515702 | 12/2008 |
| EP | 0598606 | 5/1994 | RU | 2131244 | 6/1999 |
| EP | 0636370 | 2/1995 | RU | 2354357 | 12/2007 |
| EP | 0641195 A1 | 3/1995 | RU | 2007103712 | 9/2008 |
| EP | 0647448 | 4/1995 | RU | 2007103707 | 11/2008 |
| EP | 0661045 | 7/1995 | RU | 2007132975 | 4/2009 |
| EP | 0675710 | 10/1995 | SI | 1515702 | 4/2009 |
| EP | 0682945 A2 | 11/1995 | SI | 1699440 | 11/2009 |
| EP | 0693475 A1 | 1/1996 | WO | 89/05624 | 6/1989 |
| EP | 0820693 | 1/1996 | WO | 90/03776 | 4/1990 |

| | | |
|---|---|---|
| WO | 90 03776 | 4/1990 |
| WO | 93/06723 | 4/1993 |
| WO | 93/10758 | 6/1993 |
| WO | 93/11749 | 6/1993 |
| WO | 94/06414 | 3/1994 |
| WO | 94/08567 | 4/1994 |
| WO | 95/17174 A1 | 6/1995 |
| WO | 95/22319 | 8/1995 |
| WO | WO 95/20947 | 8/1995 |
| WO | 95/30422 | 11/1995 |
| WO | 96/00066 | 1/1996 |
| WO | 96/03979 A1 | 2/1996 |
| WO | 9614058 A1 | 5/1996 |
| WO | WO 97/33566 | 9/1997 |
| WO | WO 98/20073 | 5/1998 |
| WO | 98/28698 | 7/1998 |
| WO | 98/35655 A2 | 8/1998 |
| WO | 99/12864 A1 | 3/1999 |
| WO | 99/32120 | 7/1999 |
| WO | 99/44591 | 9/1999 |
| WO | 99/48481 | 9/1999 |
| WO | 00/33835 | 6/2000 |
| WO | WO 00/40205 | 7/2000 |
| WO | 01/12230 | 2/2001 |
| WO | WO 01/08661 A2 | 2/2001 |
| WO | 01/15667 A1 | 3/2001 |
| WO | 01/52651 | 7/2001 |
| WO | 01/97783 | 12/2001 |
| WO | 02/26061 | 4/2002 |
| WO | 02/26262 | 4/2002 |
| WO | 02/26928 | 4/2002 |
| WO | 02/088217 | 11/2002 |
| WO | 03/006723 | 1/2003 |
| WO | 03/013476 | 2/2003 |
| WO | 03/013479 | 2/2003 |
| WO | WO 03/015531 A2 | 2/2003 |
| WO | 03/024430 | 3/2003 |
| WO | 03/026624 | 4/2003 |
| WO | 03 026743 A2 | 4/2003 |
| WO | 03/028698 A2 | 4/2003 |
| WO | 03/028990 | 4/2003 |
| WO | 03/031546 | 4/2003 |
| WO | 03/035053 A1 | 5/2003 |
| WO | 03/035054 | 5/2003 |
| WO | 03/035177 | 5/2003 |
| WO | WO 03/035029 A1 | 5/2003 |
| WO | 03/053417 A2 | 7/2003 |
| WO | 03/068392 | 8/2003 |
| WO | 03/092648 | 11/2003 |
| WO | WO 03/094812 A1 | 11/2003 |
| WO | 03/105808 | 12/2003 |
| WO | 2004 004693 A1 | 1/2004 |
| WO | 2004/043967 | 2/2004 |
| WO | 2004/026262 | 4/2004 |
| WO | 2004/026263 | 4/2004 |
| WO | WO 2004/093819 A2 | 4/2004 |
| WO | 2004037230 A1 | 5/2004 |
| WO | 2004037259 A1 | 5/2004 |
| WO | 2004037260 A1 | 5/2004 |
| WO | 2004/066910 | 8/2004 |
| WO | 2004/084869 | 10/2004 |
| WO | 2004/093801 | 11/2004 |
| WO | 2004/100894 | 11/2004 |
| WO | 2005/016313 | 2/2005 |
| WO | 2005/016314 | 2/2005 |
| WO | 2005/032524 | 4/2005 |
| WO | 2005/041968 | 5/2005 |
| WO | 2005 053587 | 6/2005 |
| WO | 2005/053656 A1 | 6/2005 |
| WO | 2005 055981 | 6/2005 |
| WO | 2005/063214 | 7/2005 |
| WO | 2005/065646 | 7/2005 |
| WO | 2005/066183 | 7/2005 |
| WO | 2005/102286 | 11/2005 |
| WO | 2005102294 | 11/2005 |
| WO | 2006/002883 | 1/2006 |
| WO | 2006/002884 | 1/2006 |
| WO | 2006/002886 | 1/2006 |
| WO | 2006002884 | 1/2006 |
| WO | 2006/082097 | 8/2006 |
| WO | 2006/082099 | 8/2006 |
| WO | 2007/005716 | 1/2007 |
| WO | 2007/008752 | 1/2007 |
| WO | 2007/048233 | 5/2007 |
| WO | 2007/053698 | 5/2007 |
| WO | 2007/085024 | 7/2007 |
| WO | 2008/086804 A2 | 7/2008 |
| WO | 2008/107149 A2 | 9/2008 |
| WO | 2008107149 | 9/2008 |
| WO | 2008/148798 A2 | 12/2008 |
| WO | 2009/092601 | 7/2009 |
| WO | 2009092601 | 7/2009 |
| WO | 2009/135680 | 11/2009 |
| WO | 2009135680 | 11/2009 |
| WO | 2011009602 | 1/2011 |
| WO | 2011009603 | 1/2011 |
| WO | 2011009604 | 1/2011 |

OTHER PUBLICATIONS

Bailey F.E., Journal of Applied Polymer Science, vol. 1, Issue No. 1, pp. 56-62, 1959.
Braun, et al. Angel Orthodontist, vol. 65 (5) pp. 373-377, 1995.
Bauer, et al, Lehrbuch der Pharmazeutischen Technologie, 1999.
Crowley M.M., Biomaterials 23, 2002, pp. 4241-4248.
Coppens, Pharmaceutical Technology, 62-70, Jan. 2005.
Caraballo, Journal of Controlled Release, vol. 69, pp. 345-355, 2000.
Dow Technical Data, POLYOX, Feb. 2003.
Dow Excipients Chem. of Poly. Water Soluble-Resin 2004.
Davies, et al; European Journal of Pharmaceutics and Biopharmaceutics, 67, 2007, pp. 268-276.
Efentakis M.,Pharmaceutical Development and Technology, 5 (3), pp. 339-346, 2000.
European Pharmacopoeia, pharmaceutical technical procedures, 1997, 135.
El-Sherbiny, European Polymer Journal, vol. 41, pp. 2584-2591, 2005.
Follonier N., Drug Development and Industrial Pharmacy, 20(8), pp. 1323-1339, 1994.
Follonier N., Journal of Controlled Release 36, pp. 243-250, 1995.
Fell, et al, Journal of Pharmaceutical Sciences, vol. 59, No. 5, May 1970, pp. 688-691.
Graham N.B., Poly(Ethylene Glycol) Chemistry: Biotechnical and Biomedical Applications, Chapter 17, 1992.
Griffith, Drug Administration, vol. 19, No. 1, pp. 41-42, 2003.
Hanning C.D., British Journal of Anaesthesia, 61, pp. 221-227, 1988.
Janicki S., Acta Pharm. Technol. 33 (3) 154-155, 1987.
Kim C.-J. J Pharm. Sciences 1995, 84(3), p. 303-306.
Kim, Chem. Pharm Bull. 1992, 40(10), 2800-2804.
Levina, Journal of Pharmaceutical Sciences, vol. 89, No. 6, pp. 703-723, Jun. 2000.
Levina, Drug Development and Industrial Pharmacy, vol. 28, No. 5, pp. 495-514, 2002.
Lockhart et al, "Packaging of Pharmaceuticals and Health Care Products"; Blackie Academic & Professional; First Edition 1996.
Madorsky S.L., Journal of Polymer Science, vol. 84, No. 3, Mar. 1959.
Mank R., Pharmazie 44, H. 11, pp. 773-776, 1989.
Mank R., Pharmazie 45, H. 8, pp. 592-593 1990.
Mesiha M.S., Drug Development and Industrial Pharmacy, 19(8), pp. 943-959, 1993.
Moroni A., Drug Development and Industrial Pharmacy, 21(12) pp. 1411-1428, 1995.
Miller, Nursing, pp. 50-52, Feb. 2000.
Mitchell, Special Resource, vol. 35, No. 5, pp. 535-557, 2000.
Verna, Manthena et al, Am. J. Drug Deliv. 2004: 2 (1): 43-57.
Ohnishi N., Chem. Pharm. Bull, 35(8), pp. 3511-3515, 1987.
Ozeki T., Journal of Controlled Release 58, pp. 87-95, 1999.
Pharm. Research, 1989, 6(9), 6-98.
Pharm. Research, 1991, 8(10), 8-192.
Prapaitrakul W., J. Pharm. Pharmacol. 43, pp. 377-381, 1991.
Remington's Pharmaceutical Sciences, pp. 1553-1593, Ch. 89, 1980, 16$^{th}$ Editiion.
Radko S., Applied ad Theoretical Electrophoresis 5, pp. 79-88, 1995.

Remington's Pharmaceutical Sciences 17th ed., 1418 (1985).
Rippie E.G., Journal of Pharmaceutical Sciences, vo. 58, No. 4, pp. 428-431, Apr. 1969.
Schreirs J., Polymer, vol. 32, No. 11, 1991.
Sprockel O.L., J. Pharma. Pharmacol. 42, pp. 152-157, 1990.
Stringer J.L., Journal of Controlled Release 42, pp. 195-202, 1996.
Summers et al; Journal of Pharmaceutical Sciences, vol. 66, No. 8, Aug. 1977, pp. 1172-1175.
Thoma V.K., Pharm. Ind. 51, Nr. 3, 1989.
Tipler, et al, Physics for Scientists and Engineers, 6th Edition, pp. 234-235, 2003.
US Pharmacopoeia, Chapter 1217, Aug. 1, 2008.
Wikipedia—inert gas data sheet , Dec. 2009.
Yang, Journal of Pharmaceutical Sciences, vol. 85, No. 10, Oct. 1996.
Yarbrough et al, Letters to Nature 322, 347-349 (Jul. 24, 1986) "Extraordinary effects of mortar-and-pestle grinding on microstructure of sintered alumina gel".
Maggi, L. et al., "High molecular weight polyethylene oxides (PEOs) as an alternative to HPMC in controlled release dosage form", 2000, International Journal of Pharmaceutics, 195 pp. 229-238.
Scheirs J., "Characterizing the Solid-State Thermal Oxidation of Poly (ethylene oxide) Powder", Polymer, vol. 32, No. 11, 1991.
Dachille, F. et al., "High-Pressure Phase Transformation in Laboratory Mechanical Mixers and Mortars", 1960, Nature, 186, pp. 1-2 (abstract).
2.9 Methoden der pharmazeutischen Technologie 143-144, 1997 (English translation provided).
Maggi, "Therapeutic Potential of Capsaicin-like Molecules: Studies in Animals and Humans", Life Sciences, vol. 51, pp. 1777-1781, (1992).
Handbuch der Kunststoff-Extrusionstechnik, "Grundlagen", Chapter 1.2 "Klassifizierung von Extrudern", pp. 3-7, 1989, (English Translation included).
Freed et al., "pH Control of Nucleophilic/electrophilic oxidation", International Journal of Pharmaceutics, vol. 357, pp. 180-188, (2008).

Waterman et al., "Stabilization of Pharmaceuticals to Oxidative Degradation", Pharmaceutical Development and Technology, vol. 7(1), pp. 1-32, (2002).
Jan. 6, 2011 Letter from Dr. Rick Matos, Ph.D.
Katz et al., Clin. J. Pain, 23(8): 648-660 (2007).
Arnold, "Teen Abuse of Painkiller OxyContin on the Rise," www.npr.org, Dec. 19, 2005.
Baum et al., Public Health Reports, 102(4): 426-429 (1987).
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002.
Strang, British Med. J., 302: 969 (1991).
Tompkins et al., Psychopharma., 210: 471-480 (2010).
Waters et al., Am. J. Psychiatry, 164(1): pp. 173-174 (2007).
Tablet, www.docstoc.com (2011).
Dachille, F. et al., "High-Pressure Phase Transformation in Laboratory Mechanical Mixers and Mortars", 1906., Nature, 186, pp. 1-2 (abstract).
Conversion of 18.8 kiloponds to newtons, http://www.unitconversion.org/force/newtons-to-kiloponds-conversion.html on Jul. 5, 2011.
Waltimo et al. A novel bite force recorder and maximal isometric bite force values for healthy young adults. Scand J Dent Res. 1993, vol. 101, pp. 171-175.
Waltimo et al. Maximal bite force and its association with signs and symptoms of crandiomandibular disorders in young Finnish non-patients. Acta Odonol. Scand. 1995, vol. 53, pp. 254-258.
Pharmazeutische Biologie—Drogen und ihre Inhaltsstoffe-Scharfstoffdrogen, 1982, pp. 82-92.
Stafford J. Uberzogene feste Formen, 1991, pp. 347-368.
Bauer, Coated Pharmaceutical Dosage Forms, CRC Press, 1998, pp. 1-10.

\* cited by examiner

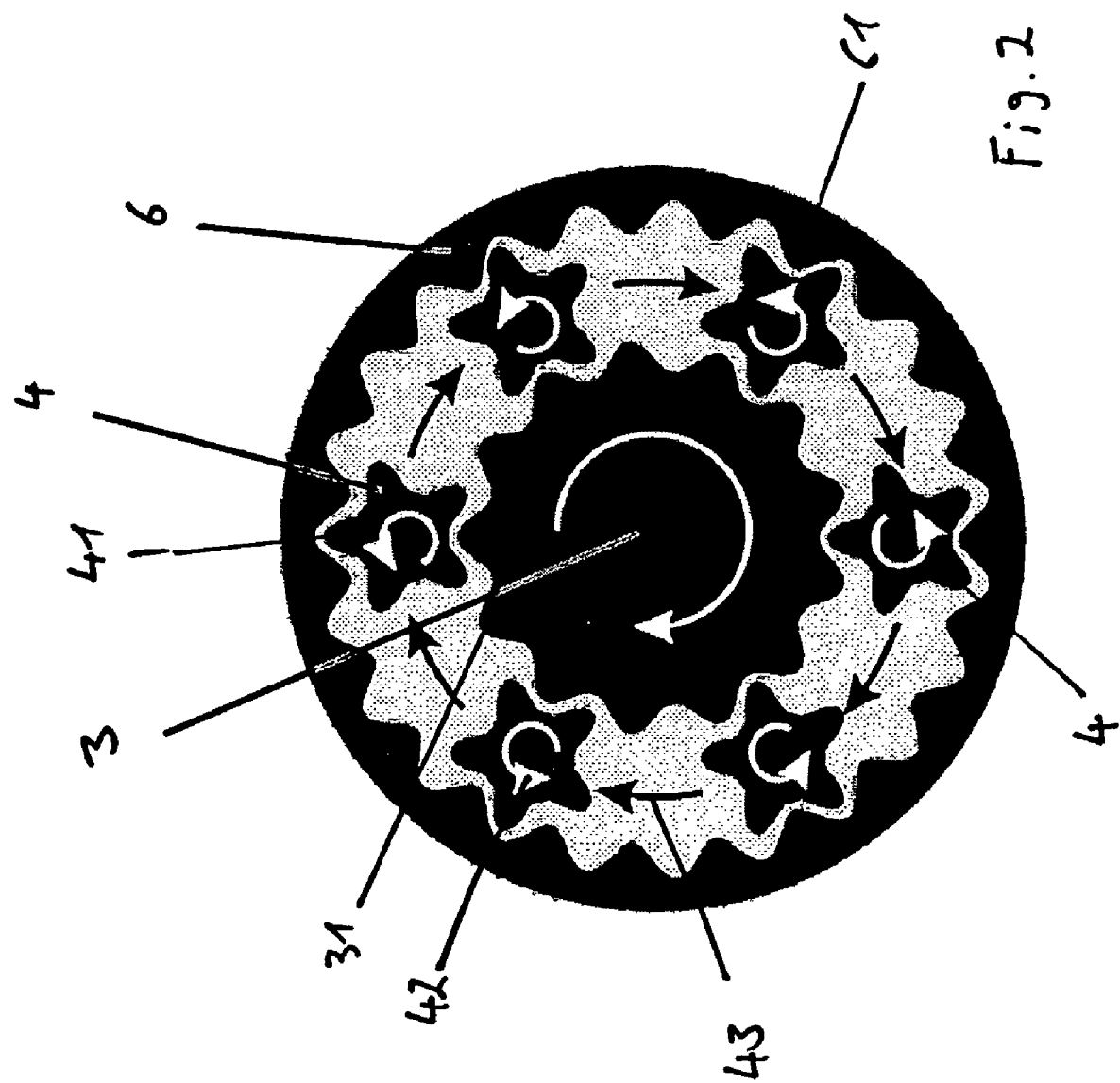

PROCESS FOR THE PRODUCTION OF AN ABUSE-PROOFED SOLID DOSAGE FORM

CROSS-REFERENCE TO RELATED APPLICATIONS

This application claims priority from German patent application No. 10 2004 032 051.9 filed on Jul. 1, 2004.

BACKGROUND OF THE INVENTION

1. Field of the Invention

The present invention relates to a process for the production of an abuse-proofed solid dosage form containing at least one active ingredient with potential for abuse and at least one synthetic or natural polymer (C) with a breaking strength of =500 N, characterised in that a mixture comprising the active ingredient and the polymer component (C) is processed by melt extrusion with the assistance of a planetary-gear extruder into formed articles which are optionally subjected to singulation and optionally to further shaping to yield the dosage form.

Many pharmaceutical active ingredients, in addition to having excellent activity in their appropriate application, also have abuse potential, i.e. they can be used by an abuser to bring about effects other than those intended. Opioids, for example, which are highly active in combating severe to very severe pain, are frequently used by abusers to induce a state of narcosis or euphoria.

In order to make abuse possible, the corresponding dosage forms, such as tablets or capsules are comminuted, for example ground in a mortar, by the abuser, the active ingredient is extracted from the resultant powder using a preferably aqueous liquid and the resultant solution, optionally after being filtered through cotton wool or cellulose wadding, is administered parenterally, in particular intravenously. An additional phenomenon of this kind of administration, in comparison with oral abuse, is a further accelerated increase in active ingredient levels giving the abuser the desired effect, namely the "kick" or "rush". This kick is also obtained if the powdered dosage form is administered abusively nasally, i.e. is sniffed. Since delayed-release dosage forms containing active ingredients with potential for abuse do not give rise to the kick desired by the abuser when taken orally even in abusively high quantities, such dosage forms are also comminuted and extracted in order to be abused.

2. Brief Description of Related Developments

U.S. Pat. No. 4,070,494 proposed adding a swellable agent to the dosage form in order to prevent abuse. When water is added to extract the active ingredient, this agent swells and ensures that the filtrate separated from the gel contains only a small quantity of active ingredient.

The multilayer tablet disclosed in WO 95/20947 is based on a similar approach to preventing parenteral abuse, said tablet containing the active ingredient with abuse potential and at least one gel former, each in different layers.

WO 03/015531 A2 discloses another approach to preventing parenteral abuse. A dosage form containing an analgesic opioid and a dye as an aversive agent is described therein. The colour released by tampering with the dosage form is intended to discourage the abuser from using the dosage form which has been tampered with.

Another known option for complicating abuse involves adding antagonists to the active ingredients to the dosage form, for example naloxone or naltexone for opioids, or compounds which cause a physiological defence response, such as for example ipecacuanha (ipecac) root.

Since, however, as in the past, it is in most cases necessary for the purposes of abuse to pulverise the dosage form, it was the object of the present invention to provide a process for the production of dosage forms containing active ingredients with potential for abuse, which, when correctly administered, ensure the desired therapeutic action, but from which the active ingredients cannot be converted into a form suitable for abuse simply by pulverisation.

SUMMARY OF THE INVENTION

This object was achieved by the provision of the process according to the invention for the production of an abuse-proofed solid dosage form containing at least one active ingredient with potential for abuse and at least one synthetic or natural polymer (C) with a breaking strength of =500 N, characterised in that a mixture comprising the active ingredient and the polymer component (C) is processed by melt extrusion with the assistance of a planetary-gear extruder into formed articles which are optionally subjected to singulation and shaping to yield the dosage form.

With the assistance of the process according to the invention using component (C) with the stated minimum breaking strength and formulation with the assistance of a planetarygear extruder, it is possible to provide a dosage form with a breaking strength of =500 N, which complicates considerably or prevents pulverisation of the dosage form with conventional means and subsequent abuse.

Preferably, component (C) is present in such quantities that the dosage form obtained according to the invention exhibits a breaking strength of at least =500 N, preferably of at least 1000 N.

As already stated, without sufficient comminution of the dosage form, non-hazardous parenteral, in particular intravenous, administration is impossible or extraction of the active ingredient takes the abuser too long, or no kick is obtained on abusive oral administration, since spontaneous release does not occur.

According to the invention, comminution is taken to mean pulverisation of the dosage form with conventional means which are available to an abuser, such as for example a pestle and mortar, a hammer, a mallet or other usual means for pulverisation by application of force.

Planetary-gear extruders are known and described inter alia in detail in Handbuch der Kunststoff-Extrusionstechnik I (1989) "Grundlagen" in Chapter 1.2 "Klassifizierung von Extrudern", pages 4 to 6. The corresponding description is hereby introduced as a reference and is deemed to be part of the disclosure.

The use of planetary-gear extruders for the production of preferably porous granules comprising a pharmaceutical active ingredient by wet pelletisation is already disclosed in WO 03/028698. This publication does not make any reference to the procedure according to the invention for the production of an abuse-proofed dosage form comprising at least one active ingredient with potential for abuse.

The dosage forms produced according to the invention with a breaking strength of at least 500 N, by which parenteral, nasal and/or oral abuse of active ingredients with potential for abuse is extensively prevented, are not therefore known from the prior art.

Active ingredients with potential for abuse, preferably pharmaceutical active ingredients with potential for abuse, are known to the person skilled in the art, as are the quantities thereof to be used, and may be protected against abuse as such, in the form of the corresponding derivatives thereof, in particular esters, ethers or amides, or in each case in the form of corresponding physiologically acceptable compounds, in particular in the form of the salts or solvates thereof, as racemates, enantiomers or stereoisomers by the process according to the invention for the production of corresponding dosage forms.

The process according to the invention is particularly suitable for the prevention of abuse of a preferably pharmaceutical active ingredient from a solid, preferably oral dosage form, which active ingredient is selected from the group comprising opioids, tranquillisers, preferably benzodiazepine; barbiturates, stimulants and further narcotics.

The process according to the invention is very particularly suitable for preventing abuse of dosage forms comprising at least one opioid, tranquilliser and/or another narcotic selected from the group consisting N-{1-[2-(4-ethyl-5-oxo-2-tetrazolin-1-yl)ethyl]-4-methoxymethyl-4-piperidyl}propionanilide (alfentanil), allyiprodine, alphaprodine, anileridine, bemidone, benzylmorphine, bezitramide, 17-cyclopropylmethyl-4,5a-epoxy-7a[(S)-1-hydroxy-1,2,2-trimethyl-propyl]-6-methoxy-6,14-endo-ethanomorphinan-3-ol (buprenorphine), butorphanol, carfentanil, clonitazene, (−)-methyl-[3β-benzoyloxy-2β(1aH,5aH)-tropane carboxylate] (cocaine), 4,5a-epoxy-3-methoxy-17-methyl-7-morphinen-6a-ol (codeine), 5-(1-cyclohexenyl)-5-ethyl barbituric acid (cyclobarbital), cyclorphan, cyprenorphine, 7-chloro-5-(2-chlorophenyl)-1H-1,4-benzodiazepin-2(3H)-one (delorazepam), desomorphine, dextromoramide, (+)-(1-benzyl-3-dimethylamino-2-methyl-1-phenylpropyl)propionate (dextropropoxyphene), dezocine, diampromide, diamorphone, 4,5a-epoxy-3-methoxy-17-methyl-6a-morphinanol (dihydrocodeine), 4,5a-epoxy-17-methyl-3,6a-morphinandiol (dihydromorphine), dimenoxadol, dimephetamol, dimethylthiambutene, dioxaphetylbutyrate, dipipanone, dihydromorphone, eptazocine, ethoheptazine, ethylmethylthiambutene, 4,5a-epoxy-3-ethoxy-17-methyl-7-morphinen-6a-ol (ethylmorphine), etonitazene, 4,5a-epoxy-7a-(1-hydroxy-1-methylbutyl)-6-methoxy-17-methyl-6,14-endo-etheno-morphinan-3-ol (etorphine), fenpipramide, N-(1-phenethyl-4-piperidyl)propionanilide (fentanyl), heroin, 4,5a-epoxy-3-methoxy-17-methyl-6-morphinanone (hydrocodone), 4,5a-epoxy-3-hydroxy-17-methyl-6-morphinanone (hydromorphone), hydroxypethidine, isomethadone, hydroxymethylmorphinan, 1-[4-(3-hydroxyphenyl)-1-methyl-4-piperidyl]-1-propanone (ketobemidone), (3S,6S)-6-dimethylamino-4,4-diphenylheptan-3-yl acetate (levacetylmethadol (LAAM)), (−)-6-dimethylamino-4,4-diphenol-3-heptanone (levomethadone), (−)-17-methyl-3-morphinanol (levorphanol), levophenacylmorphane, levoxemacin, lofentanil, meperidine, 2-methyl-2-propyltrimethylene dicarbamate (meprobamate), meptazinol, metazocine, methylmorphine, 4,5a-epoxy-17-methyl-7-morphinen-3,6a-diol (morphine), myrophine, nalbuphene, nalorphine, narceine, nicomorphine, 6-dimethylamino-4,4-diphenyl-3-hexanone (normethadone), normorphine, norpipanone, the exudation for the plants belonging to the species Papaver somniferum (opium), 4,5a-epoxy-14-hydroxy-3-methoxy-17-methyl-6-morphinanone (oxycodone), oxymorphone, plants and parts of plants belonging to the species Papaver somniferum (including the subspecies setigerum) (Papaver somniferum), papaveretum, 1,2,3,4,5,6-hexahydro-6,11-dimethyl-3-(3-methyl-2-butenyl)-2,6-methano-3-benzazocin-8-ol (pentazocine), ethyl-(1-methyl-4-phenyl-4-piperidinecarboxylate) (pethidine), phenadoxone, phenomorphane, phenazocine, phenoperidine, piminodine, pholcodeine, 1'-(3-cyano-3,3-diphenylpropyl)[1,4'-bipiperidine]-4'-carboxamide (piritramide), proheptazine, promedol, properidine, propoxyphene, methyl {3-[4-methoxycarbonyl-4-(N-phenylpropanamido)piperidino]-propanoate} (remifentanil), N-{4-methoxymethyl-1-[2-(2-thienyl)ethyl]-4-piperidyl}propionanilide (sufentanil), ethyl (2-dimethylamino-1-phenyl-3-cyclohexene-1-carboxylate) (tilidine, cis and trans), tramadol, (1R,2R,4S)-2-(dimethylamino)methyl-4-(p-fluorobenzyloxy)-1-(m-methoxyphenyl)cyclohexanol, (1R,2R)-3-(3-dimethylamino-1-ethyl-2-methyl-propyl)phenol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclohexane-1,3-diol, 3-(2-dimethylaminomethyl-1-hydroxy-cyclohexyl)phenyl 2-(4-isobutoxy-phenyl)propionate, 3-(2-dimethylaminomethyl-1-hydroxy-cyclohexyl)phenyl 2-(6-methoxy-naphthalen-2-yl)propionate, 3-(2-dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl)propionate, (RR-SS)-2-acetoxy-4-trifluoromethyl-benzoic acid 3-(2-dimethylaminomethyl-1-hydroxy-cyclohexyl)-phenyl ester, (RR-SS)-2-hydroxy-4-trifluoromethyl-benzoic acid 3-(2-dimethylaminomethyl-1-hydroxy-cyclohexyl)-phenyl ester, (RR-SS)-4-chloro-2-hydroxy-benzoic acid 3-(2-dimethylaminomethyl-1-hydroxy-cyclohexyl)-phenyl ester, (RR-SS)-2-hydroxy-4-methyl-benzoic acid 3-(2-dimethylaminomethyl-1-hydroxy-cyclohexyl)-phenyl ester, (RR-SS)-2-hydroxy-4-methoxy-benzoic acid 3<2-dimethylaminomethyl-1-hydroxy-cyclohexyl phenyl ester, (RR-SS)-2-hydroxy-5-nitro-benzoic acid 3-(2-dimethylaminomethyl-1-hydroxy-cyclohexyl)-phenyl ester, (RR-SS)-2',4'-difluoro-3-hydroxy-biphenyl-4-carboxylic acid 3-(2-dimethylaminomethyl-1-hydroxy-cyclohexyl)-phenyl ester together with corresponding stereoisomeric compounds, in each case the corresponding derivatives thereof, in particular amides, esters or ethers, and in each case the physiologically acceptable compounds thereof, in particular the salts and solvates thereof.

Particularly preferably, the compounds (1R2R)-3-(3-dimethylamino-1-ethyl-2-methyl-propyl)phenol, (1R,2R,4S)-2-[(dimethylamino)methyl-4-(p-fluorobenzyloxy)-1-(m-methoxyphenyl)-cyclohexanol or the stereoisomeric compounds thereof or the physiologically acceptable compounds thereof, in particular the hydrochlorides thereof, the derivatives thereof, such as esters or ethers may be protected against abuse according to the invention. Processes for the production of these compounds are known for example from EP-A-693475 and EP-A-780369. The corresponding descriptions are hereby introduced as a reference and are deemed to be part of the disclosure.

Active ingredients which may particularly preferably also be protected against abuse according to the invention are opioids, such as oxycodone, morphine, hydromorphone, tramadol or the physiologically acceptable salts thereof, preferably hydrochlorides.

Furthermore, particularly preferably at least one opioid active ingredient selected from among group comprising (2R,3R)-1-dimethylamino-3-(3-methoxy-phenyl)-2-methyl-pentan-3-ol, (1RS,3RS,6RS)-6-dimethylaminomethyl-1-(3-methoxy-phenyl)-cyclohexane-1,3-diol, (1R,2R)-3-(2-dimethylaminomethyl-cyclohexyl)phenol, the physiologically acceptable salts thereof, preferably hydrochlorides, physiologically acceptable enantiomers, stereoisomers, diastereomers and racemates and the physiologically acceptable derivatives thereof, preferably ethers, esters or amides, may be protected against abuse according to the invention.

In the process according to the invention, at least one synthetic or natural polymer (C) is used which has a breaking strength of =500 N measured using the method disclosed in the present application. The polymer is preferably used in a quantity of at least 20 wt. %, preferably at least 35 wt. %, particularly preferably 50 to 99.9 wt. %, relative to the total weight of the dosage form.

At least one polymer selected from the group comprising polymethylene oxide, polyethylene oxide, polypropylene oxide, polyethylene, polypropylene, polyvinyl chloride, polycarbonate, polystyrene, polyacrylate, copolymers thereof, and mixtures of at least two of the stated polymers is preferably used for this purpose. The polymers are distinguished by a molecular weight of at least 0.5 million, determined by rheological measurements. Very particularly preferred are thermoplastic polyalkylene oxides, such as polyethylene oxides, with a molecular weight of at least 0.5 million, preferably of at least 1 million, particularly preferably of at least 5 million, preferably up to 15 million, determined by rheological measurements. These polymers have a viscosity at 25° C. of 4500 to 17600 cP, measured on a 5 wt. % aqueous solution using a model RVF Brookfield viscosimeter (spindle no. 2/rotational speed 2 rpm), of 400 to 4000 cP, measured on a 2 wt. % aqueous solution using the stated viscosimeter (spindle no. 1 or 3/rotational speed 10 rpm) or of 1650 to 10000 cP, measured on a 1 wt. % aqueous solution using the stated viscosimeter (spindle no. 2/rotational speed 2 rpm).

The polymers are preferably used in powder form.

In order to achieve the necessary breaking strength with the process according to the invention, it is furthermore possible additionally to use at least one natural or synthetic wax (D) with a breaking strength, measured using the method disclosed in the present application, of at least 500 N. Waxes with a softening point of at least 60° C. are preferred. Carnauba wax and beeswax are particularly preferred. Carnauba wax is very particularly preferred. Carnauba wax is a natural wax which is obtained from the leaves of the carnauba palm and has a softening point of at most 90° C.

When the wax component is additionally used, it is used together with at least one polymer (C) in quantities such that the dosage form has a breaking strength of at least 500 N.

Surprisingly, by extruding a mixture comprising the active ingredient with potential for abuse and with the assistance of a planetary-gear extruder using the melt method, it is possible simply and reproducibly to achieve the necessary breaking strength of =500 N, which ensures that pulverisation of the dosage form is impossible with conventional means and thus subsequent abuse is complicated considerably or prevented.

To perform the process according to the invention, at least one active ingredient with potential for abuse, the component or components (C) and optionally a wax (D), optionally at least one of the further optionally present abuse-preventing components (a) to (f) listed below and optionally present auxiliary substances such as antioxidants, plasticisers and/or delayed-release auxiliary substances are processed with the assistance of a planetary-gear extruder to yield the dosage form according to the invention.

Below, the use of planetary-gear extruder in the process according to the invention is explained with reference to FIGS. 1 and 2. These explanations are given merely by way of example and do not restrict the general concept of the invention.

FIG. 2 shows the mode of operation of the planetary-gear extruder.

Figure 1:
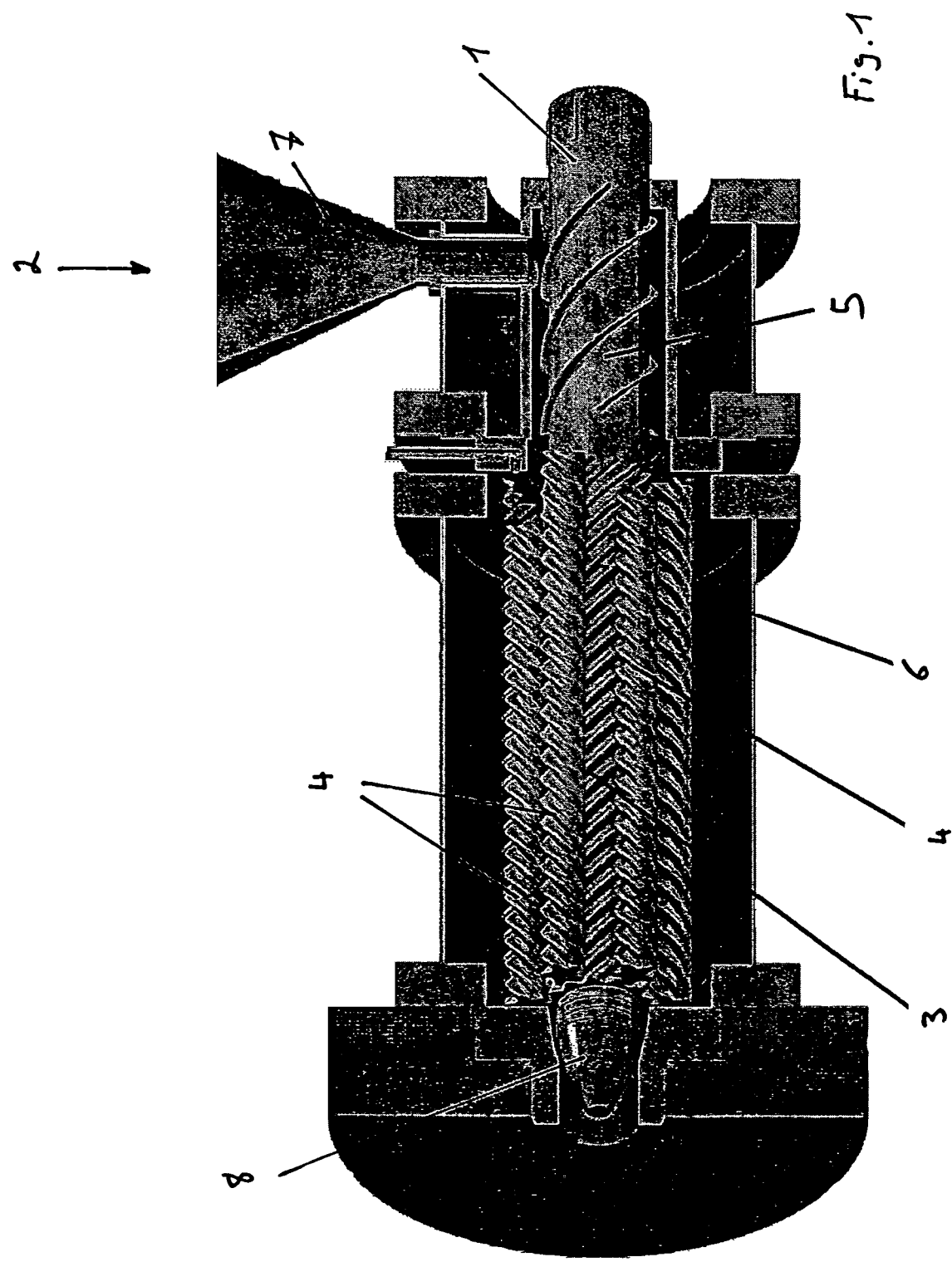
FIG. 1 shows a section through a planetary-gear extruder.

FIG. 1 shows a planetary-gear extruder which may be used in the process according to the invention. This extruder substantially comprises a shaft 1, which, relative to the transport directon of the mixture of the components listed above to be extruded, is initially constructed as a feed screw 5 and subsequently as the central spindle 3 of the planetary-gear extruder. Around the central spindle 3 there are preferably arranged three to seven planetary spindles 4, which are in turn surrounded by a casing in the form of a housing 6.

In the planetary-gear extruder, extrusion of the composition used in the process according to the invention for the production of a pharmaceutical dosage form preferably proceeds as follows, with reference to FIG. 1. As shown by arrow 2, the components to be extruded are apportioned by the apportioning unit 7 in the area of the feed screw 5 and conveyed by the rotation thereof (drive not shown) in the direction of the central spindle 3. The person skilled in the art will understand that it is possible to mix the starting materials (components) in the area of the feed screw. However, it is also possible to premix the components of the dosage form and to apportion this mixture via the apportioning unit 7 in the area of the feed screw 5. The mixture is conveyed into the feed zone of the planeta-gear extruder. By heating at least to the softening point of component (C), the mixture is melted and the molten mixture is conveyed into the area of the central spindle by the interaction of the central spindle 3 and the planetary spindles 4, further homogenised, compressed or compacted and extruded through the die 8 as an extruded strand or extruded strands, depending on how many bores the die comprises. The die geometry or the geometry of the bores is freely selectable. Thus, the die or the bores may exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. The extrusion die may also take the form of a slot die. Preferably, the die or the bores have a round cross-section. Both the casing 6 of the planetary-gear extruder used according to the invention and the central spindle may be heated or cooled. The corresponding temperature adjustment, i.e. heating or cooling, is so arranged that the mixture to be extruded exhibits an average temperature corresponding to the softening temperature of component (C) and does not rise above a temperature at which the active ingredient with potential for abuse may be damaged. Preferably, the temperature of the mixture to be extruded is adjusted to below 180° C., preferably below 150° C., but at least to the softening temperature of component (C).

After extrusion of the molten mixture and optional cooling of the extruded strand or extruded strands, the extrudates are comminuted (not shown in FIG. 1). This comminution may preferably be performed by cutting up the extrudates by means of revolving or rotating knives, water jet cutters, wires, blades or with the assistance of laser cutters.

Optionally after further cooling of the comminuted extrudates, which are preferably present in the form of disks, they are optionally re-shaped into the final shape of the dosage form, wherein they may be exposed to heat again if necessary.

This shaping for example into tablets may proceed in that the plastic extrudate is shaped with press moulding with the assistance of two contrarotating rolls preferably with mutually opposing recesses in the roll sleeve for plastification, the construction of which recesses determines the tablet shape.

However, it is also possible to form the tablets from the singulated extrudates in each case with the assistance of an optionally heated die and at least one shaping punch. To this end, the cylindrical granules obtained after comminution of the extruded strand may preferably be used. Apart from being press-moulded into tablets, these granules or other multiparticulate shapes obtained, such as pellets or spheroids, may also be packaged into capsules in order to be used as a dosage form produced according to the invention.

In a further preferred embodiment, the extruded strands extruded through a plurality of bores in the extrusion die may, after cooling thereof, optionally be brought together by interlacing or wrapping in the manner of rope production to yield a thicker strand than the individual extruded strands. This strand may optionally be further processed by solvent attack with a suitable solvent or by heating to the softening point of component (C) and optionally removing the solvent in accordance with the above-stated comminution and shaping of an individual strand.

FIG. 2 shows a cross-section through the planetary-gear extruder. Around the rotating central spindle 3 there are arranged at least three, in the case illustrated 6, planetary spindles 4, whose flanks 41 interact on the one hand with the flank 31 of the central spindle 4 and on the other hand with the flanks 61 of the casing 6 of the planetary-gear extruder. Through rotation of the central spindle 3 and rolling of the respective flanks over one another, the planetary spindles 4 each rotate round their own axis, as shown by arrow 42, and round the central spindle 4, as shown by arrow 43. In this way, the compression or compaction sought according to the invention of the component mixture used according to the invention of the dosage forms produced according to the invention is achieved.

If necessary, the planetary-gear extruder used may comprise not only an extrusion area but also at least one further area, so that the mixture to be extruded may optionally also be degassed.

The process according to the invention may be performed discontinuously or continuously, preferably continuously.

The dosage forms obtained by the process according to the invention are distinguished as stated in that they cannot be pulverised due to their hardness. This virtually rules out oral or parenteral, in particular intravenous or nasal abuse. However, in order to prevent any possible abuse of the dosage forms obtained by the production process according to the invention in the event of comminution and/or pulverisation which possibly occur nonetheless due to extraordinary force, in a preferred embodiment these dosage forms may contain further abuse-complicating or -preventing agents as auxiliary substances.

Thus, the dosage form obtained according to the invention may comprise, in addition to at least one active ingredient with potential for abuse, at least one polymer component (C) and optionally one wax (D), at least one of the following components:
(a) at least one substance which irritates the nasal passages and/or pharynx,
(b) at least one viscosity-increasing agent, which, with the assistance of a necessary minimum quantity of an aqueous liquid, preferably as an aqueous extract obtained from the dosage form, forms a gel which preferably remains visually distinguishable when introduced into a further quantity of an aqueous liquid,
(c) at least one antagonist for each of the active ingredients with potential for abuse,
(d) at least one emetic,
(e) at least one dye as an aversive agent,
(f) at least one bitter substance.

Components (a) to (f) are additionally each individually suitable for abuse-proofing the dosage forms obtained by the process according to the invention. Accordingly, component (a) is preferably suitable for proofing the dosage form against nasal, oral and/or parenteral, preferably intravenous, abuse, component (b) is preferably suitable for proofing against parenteral, particularly preferably intravenous and/or nasal abuse, component (c) is preferably suitable for proofing against nasal and/or parenteral, particularly preferably intravenous, abuse, component (d) is preferably suitable for proofing against parenteral, particularly preferably intravenous, and/or oral and/or nasal abuse, component (e) is suitable as a visual deterrent against oral or parenteral abuse and component (f) is suitable for proofing against oral or nasal abuse. Combined use according to the invention of at least one of the above-stated components makes it possible still more effectively to prevent abuse of dosage forms obtained by the process according to the invention.

For example, the dosage form obtained according to the invention may also comprise two or more of components (a)-(f) in a combination, preferably (a), (b) and optionally (c) and/or (f) and/or (e) or (a), (b) and optionally (d) and/or (f) and/or (e).

In another embodiment, the dosage form according to the invention may comprise all of components (a)-(f).

If the dosage form obtained by the process according to the invention comprises an abuse-preventing component (a), substances which irritate the nasal passages and/or pharynx which may be considered according to the invention are any substances which, when administered abusively via the nasal passages and/or pharynx, bring about a physical reaction which is either so unpleasant for the abuser that he/she does not wish to or cannot continue administration, for example burning, or physiologically counteracts taking of the corresponding active ingredient, for example due to increased nasal secretion or sneezing. These substances which conventionally irritate the nasal passages and/or pharynx may also bring about a very unpleasant sensation or even unbearable pain when administered parenterally, in particular intravenously, such that the abuser does not wish to or cannot continue taking the substance.

Particularly suitable substances which irritate the nasal passages and/or pharynx are those which cause burning, itching, an urge to sneeze, increased formation of secretions or a combination of at least two of these stimuli. Appropriate substances and the quantities thereof which are conventionally to be used are known per se to the person skilled in the art or may be identified by simple preliminary testing.

The substance which irritates the nasal passages and/or pharynx of component (a) is preferably based on one or more constituents or one or more plant parts of at least one hot substance drug.

Corresponding hot substance drugs are known per se to the person skilled in the art and are described, for example, in "Pharmazeutische Biologie—Drogen und ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure. The dosage form obtained by the process according to the invention may preferably contain the plant parts of the corresponding hot substance drugs in a quantity of 0.01 to 30 wt. %, particularly preferably of 0.1 to 0.5 wt. %, in each case relative to the total weight of the dosage unit.

If one or more constituents of corresponding hot substance drugs are used, the quantity thereof in a dosage unit obtained by the process according to the invention preferably amounts to 0.001 to 0.005 wt. %, relative to the total weight of the dosage unit.

A dosage unit is taken to mean a separate or separable administration unit, such as for example a tablet or a capsule.

One or more constituents of at least one hot substance drug selected from the group comprising *Allii sativi bulbus* (garlic), *Asari rhizoma cum herba* (Asarum root and leaves), *Calami rhizoma* (calamus root), *Capsici fructus* (capsicum), *Capsici fructus acer* (cayenne pepper), *Curcumae longae rhizoma* (turmeric root), *Curcumae xanthorrhizae rhizoma* (Javanese turmeric root), *Galangae rhizoma* (galangal root), *Myristicae semen* (nutmeg), *Piperis nigri fructus* (pepper), *Sinapis albae semen* (white mustard seed), *Sinapis nigri semen* (black mustard seed), *Zedoariae rhizoma* (zedoary root) and *Zingiberis rhizoma* (ginger root), particularly preferably from the group comprising *Capsici fructus* (capsicum), *Capsici fructus acer* (cayenne pepper) and *Piperis nigri fructus* (pepper) may preferably be added as component (a) to the dosage form obtained according to the invention.

The constituents of the hot substance drugs preferably comprise o-methoxy(methyl)phenol compounds, acid amide compounds, mustard oils or sulfide compounds or compounds derived therefrom.

Particularly preferably, at least one constituent of the hot substance drugs is selected from the group consisting of myristicin, elemicin, isoeugenol, a-asarone, safrole, gingerols, xanthorrhizol, capsaicinoids, preferably capsaicin, capsaicin derivatives, such as N-vanillyl-9E-octadecenamide, dihydrocapsaicin, nordihydrocapsaicin, homocapsaicin, norcapsaicin and nomorcapsaicin, piperine, preferably trans-piperine, glucosinolates, preferably based on non-volatile mustard oils, particularly preferably based on p-hydroxybenzyl mustard oil, methylmercapto mustard oil or methylsulfonyl mustard oil, and compounds derived from these constituents.

Another option for preventing abuse of the dosage form obtained according to the invention consists in adding at least one viscosity-increasing agent as a further abuse-preventing component (b) to the dosage form, which, with the assistance of a necessary minimum quantity of an aqueous liquid, forms a gel with the extract obtained from the dosage form, which gel is virtually impossible to administer safely and preferably remains visually distinguishable when introduced into a further quantity of an aqueous liquid.

For the purposes of the present invention visually distinguishable means that the active ingredient-containing gel formed with the assistance of a necessary minimum quantity of aqueous liquid, when introduced, preferably with the assistance of a hypodermic needle, into a further quantity of aqueous liquid at 37° C., remains substantially insoluble and cohesive and cannot straightforwardly be dispersed in such a manner that it can safely be administered parenterally, in particular intravenously. The material preferably remains visually distinguishable for at least one minute, preferably for at least 10 minutes.

The increased viscosity of the extract makes it more difficult or even impossible for it to be passed through a needle or injected. If the gel remains visually distinguishable, this means that the gel obtained on introduction into a further quantity of aqueous liquid, for example by injection into blood, initially remains in the form of a largely cohesive thread, which, while it may indeed be broken up mechanically into smaller fragments, cannot be dispersed or even dissolved in such a manner that it can safely be administered parenterally, in particular intravenously. In combination with at least one optionally present component (a) or c to (e), this additionally leads to unpleasant burning, vomiting, bad flavour and/or visual deterrence.

Intravenous administration of such a gel would therefore most probably result in serious damage to the health of the abuser.

In order to verify whether a viscosity-increasing agent is suitable as component (b) for use in the dosage form obtained according to the invention, the active ingredient is mixed with the viscosity-increasing agent and suspended in 10 ml of water at a temperature of 25° C. If this results in the formation of a gel which fulfils the above-stated conditions, the corresponding viscosity-increasing agent is suitable for preventing or averting abuse of the dosage forms obtained according to the invention.

If component (b) is added to the dosage form obtained according to the invention, one or more viscosity-increasing agents are used which are selected from the group consisting of microcrystalline cellulose with 11 wt. % carboxymethylcellulose sodium (Avicel® RC 591), carboxymethylcellulose sodium (Blanose®, CMC-Na C300P®, Frimulsion BLC-5®, Tylose C300 P®), polyacrylic acid (Carbopol® 980 NF, Carbopol® 981), locust bean flour (Cesagum® LA-200, Cesagum® LID/150, Cesagum® LN-1), pectins such as citrus pectin (Cesapectine HM Medium Rapid Set), apple pectin, pectin from lemon peel, waxy maize starch (C*Gel 04201®), sodium alginate (Frimulsion ALG (E401)®), guar flour (Frimulsion BM®, Polygum 26/1-75®), iota carrageenan (Frimulsion D021®), karaya gum, gellan gum (Kelcogel F®, Kelcogel LT100®), galactomannan (Meyprogat 150®), tara stone flour (Polygum 43/1®), propylene glycol alginate (Protanal-Ester SD-LB®), sodium hyaluronate, tragacanth, tara gum (Vidogum SP 200®), fermented polysaccharide welan gum (K1A96), xanthan gum (Xantural 180®). Xanthans are particularly preferred. The names stated in brackets are the trade names by which the materials are known commercially. In general, a quantity of 0.1 to 5 wt. % of the viscosity-increasing agent(s) is sufficient to fulfil the above-stated conditions.

The component (b) viscosity-increasing agents, where provided, are preferably present in the dosage form obtained according to the invention in quantities of =5 mg per dosage unit, i.e. per administration unit.

In a particularly preferred embodiment of the present invention, the viscosity-increasing agents used as component (b) are those which, on extraction from the dosage form with the necessary minimum quantity of aqueous liquid, form a gel which encloses air bubbles. The resultant gels are distinguished by a turbid appearance, which provides the potential abuser with an additional optical warning and discourages him/her from administering the gel parenterally.

It is also possible to formulate the viscosity-increasing agent and the other constituents in the dosage form obtained according to the invention in a mutually spatially separated arrangement.

In order to discourage and prevent abuse, the dosage form obtained according to the invention may furthermore comprise component (c), namely one or more antagonists for the active ingredient or active ingredients with potential for abuse, wherein the antagonists are preferably spatially separated from the remaining constituents of the dosage form obtained according to the invention and, when correctly used, do not exert any effect.

Suitable antagonists for preventing abuse of the active ingredients are known per se to the person skilled in the art and may be present in the dosage form obtained according to the invention as such or in the form of corresponding derivatives, in particular esters or ethers, or in each case in the form of corresponding physiologically acceptable compounds, in particular in the form of the salts or solvates thereof.

If the active ingredient present in the dosage form is an opioid, the antagonist used is preferably an antagonist selected from the group comprising naloxone, naltrexone, nalmefene, nalide, nalmexone, nalorphine or naluphine, in each case optionally in the form of a corresponding physiologically acceptable compound, in particular in the form of a base, a salt or solvate. The corresponding antagonists, where component (c) is provided, are preferably used in a quantity of =10 mg, particularly preferably in a quantity of 10 to 100 mg, very particularly preferably in a quantity of 10 to 50 mg per dosage form, i.e. per administration unit.

If the dosage form obtained according to the invention comprises a stimulant as active ingredient, the antagonist is preferably a neuroleptic, preferably at least one compound selected from the group consisting of haloperidol, promethazine, fluphenazine, perphenazine, levomepromazine, thioridazine, perazine, chlorpromazine, chlorprothixine, zuclopentixol, flupentixol, prothipendyl, zotepine, benperidol, pipamperone, melperone and bromperidol.

The dosage form obtained according to the invention preferably comprises these antagonists in a conventional therapeutic dose known to the person skilled in the art, particularly preferably in a quantity of twice to three times the conventional dose per administration unit.

If the combination to discourage and prevent abuse of the dosage form obtained according to the invention comprises component (d), it may comprise at least one emetic, which is preferably present in a spatially separated arrangement from the other components of the dosage form obtained according to the invention and, when correctly used, is intended not to exert its effect in the body.

Suitable emetics for preventing abuse of an active ingredient are known to the person skilled in the art and may be present in the dosage form obtained according to the invention as such or in the form of corresponding derivatives, in particular esters or ethers, or in each case in the form of corresponding physiologically acceptable compounds, in particular in the form of the salts or solvates thereof.

An emetic based on one or more constituents of ipecacuanha (ipecac) root, preferably based on the constituent emetine may preferably be considered in the dosage form obtained according to the invention, as are, for example, described in "Pharmazeutische Biologie—Drogen und ihre Inhaltsstoffe" by Prof. Dr. Hildebert Wagner, 2nd, revised edition, Gustav Fischer Verlag, Stuttgart, New York, 1982. The corresponding literature description is hereby introduced as a reference and is deemed to be part of the disclosure.

The dosage form obtained according to the invention may preferably comprise the emetic emetine as component (d), preferably in a quantity of =10 mg, particularly preferably of =20 mg and very particularly preferably in a quantity of =40 mg per dosage form, i.e. administration unit.

Apomorphine may likewise preferably be used as an emetic for additional abuse-proofing, preferably in a quantity of preferably =3 mg, particularly preferably of =5 mg and very particularly preferably of =7 mg per administration unit.

If the dosage form obtained according to the invention contains component (e) as an additional abuse-preventing auxiliary substance, the use of such a dye brings about an intense coloration of a corresponding aqueous solution, in particular when the attempt is made to extract the active ingredient for parenteral, preferably intravenous administration, which coloration may act as a deterrent to the potential abuser. Oral abuse, which conventionally begins by means of aqueous extraction of the active ingredient, may also be prevented by this coloration. Suitable dyes and the quantities required for the necessary deterrence may be found in WO 03/015531, wherein the corresponding disclosure should be deemed to be part of the present disclosure and is hereby introduced as a reference.

If the dosage form obtained according to the invention contains component (f) as a further abuse-preventing auxiliary substance, this addition of at least one bitter substance and the consequent impairment of the flavour of the dosage form additionally prevents oral and/or nasal abuse.

Suitable bitter substances and the quantities effective for use may be found in US-2003/0064099 A1, the corresponding disclosure of which should be deemed to be the disclosure of the present application and is hereby introduced as a reference. Suitable bitter substances are preferably aromatic oils, preferably peppermint oil, eucalyptus oil, bitter almond oil, menthol, fruit aroma substances, preferably aroma substances from lemons, oranges, limes, grapefruit or mixtures thereof, and/or denatonium benzoate.

The solid dosage form obtained according to the invention is suitable for oral or rectal administration, preferably for oral administration, to humans and animals.

The orally administrable dosage form obtained according to the invention may, as stated, be present in multiparticulate form, preferably in the form of granules, preferably in cylindrical form, spheroids, beads or pellets, optionally packaged into capsules or press-moulded into tablets. Preferably, the multiparticulate shapes exhibit a minimum size of 0.1 mm to 10 cm, particularly preferably in the range from 0.1 to 3.0 mm, particularly preferably in the range from 0.5 to 2 mm.

In a further preferred embodiment, the dosage form obtained according to the invention assumes the form of a tablet, a capsule or is in the form of an oral osmotic therapeutic system (OROS), preferably if at least one further abuse-preventing component (a)-(f) is also present.

If components (c) and/or (d) and/or (f) are present in the dosage form obtained according to the invention, care must be taken to ensure that they are formulated in such a manner or are present in such a low dose that, when correctly administered, the dosage form is able to bring about virtually no effect which impairs the patient or the efficacy of the active ingredient.

If the dosage form produced according to the invention contains component (d) and/or (f), the dosage must be selected such that, when correctly orally administered, no negative effect is caused. If, however, the intended dosage of the dosage form is exceeded inadvertently, in particular by children, or in the event of abuse, nausea or an inclination to vomit or a bad flavour are produced. The particular quantity of component (d) and/or (f) which can still be tolerated by the patient in the event of correct oral administration may be determined by the person skilled in the art by simple preliminary testing.

If, however, irrespective of the fact that the dosage form produced according to the invention is virtually impossible to pulverise, the dosage form containing the components (c) and/or (d) and/or (f) is provided with protection, these components should preferably be used at a dosage which is sufficiently high that, when abusively administered, they bring about an intense negative effect on the abuser. This is preferably achieved by spatial separation of at least the active ingredient or active ingredients from components (c) and/or (d) and/or (f), wherein the active ingredient or active ingredients is/are present in at least one subunit (X) and components (c) and/or (d) and/or (f) is/are present in at least one subunit (Y), and wherein, when the dosage form is correctly administered, components (c), (d) and (f) do not exert their effect on taking and/or in the body and the remaining components of the formulation, in particular component (C), are identical.

If the dosage form according to the invention comprises at least 2 of components (c) and (d) or (f), these may each be present in the same or different subunits (Y). Preferably, when present, all the components (c) and (d) and (f) are present in one and the same subunit (Y).

For the purposes of the present invention, subunits are solid formulations, which in each case, apart from conventional auxiliary substances known to the person skilled in the art, contain the active ingredient(s), preferably also at least one polymer (C) and optionally at least one of the optionally present components (a) and/or (b) and/or (e) or preferably in each case at least one polymer (C) and the antagonist(s) and/or emetic(s) and/or component (e) and/or component (f) and optionally at least one of the optionally present components (a) and/or (b). Care must here be taken to ensure that each of the subunits is formulated in accordance with the above-stated process according to the invention, if the mechanical skill is desired or required.

One substantial advantage of the separated formulation of active ingredients from components (c) or (d) or (f) in subunits (X) and (Y) of the dosage form produced according to the invention is that, when correctly administered, components (c) and/or (d) and/or (f) are hardly released on taking and/or in the body or are released in such small quantities that they exert no effect which impairs the patient or therapeutic success or, on passing through the patient's body, they are only liberated in locations where they cannot be sufficiently absorbed to be effective. When the dosage form is correctly administered, preferably hardly any of components (c) and/or (d) and/or (f) is released into the patient's body or they go unnoticed by the patient.

The person skilled in the art will understand that the above-stated conditions may vary as a function of the particular components (c), (d) and/or (f) used and of the formulation of the subunits or the dosage form. The optimum formulation for the particular dosage form may be determined by simple preliminary testing. What is vital, if necessary for abuse prevention, is that each subunit contains the polymer (C) and has been formulated in the stated manner and produced according to the invention.

Should, contrary to expectations, the abuser succeed in comminuting such a dosage form obtained according to the invention, which comprises components (c) and/or (e) and/or (d) and/or (f) in subunits (Y), for the purpose of abusing the active ingredient and obtain a powder which is extracted with a suitable extracting agent, not only the active ingredient but also the particular component (c) and/or (e) and/or (f) and/or (d) will be obtained in a form in which it cannot readily be separated from the active ingredient, such that when the dosage form which has been tampered with is administered, in particular by oral and/or parenteral administration, it will exert its effect on taking and/or in the body combined with an additional negative effect on the abuser corresponding to component (c) and/or (d) and/or (f) or, when the attempt is made to extract the active ingredient, the coloration will act as a deterrent and so prevent abuse of the dosage form.

A dosage form in which the active ingredient or active ingredients is/are spatially separated from components (c), (d) and/or (e), preferably by formulation in different subunits, may be formulated according to the invention in many different ways, wherein the corresponding subunits of such a dosage form may each be present in any desired spatial arrangement relative to one another, provided that the above-stated conditions for the release of components (c) and/or (d) are fulfilled.

The person skilled in the art will understand that component(s) (a) and/or (b) which are optionally also present may preferably be formulated in the dosage form produced according to the invention both in the particular subunits (X) and (Y) and in the form of independent subunits corresponding to subunits (X) and (Y), provided that neither the abuse-proofing nor the active ingredient release in the event of correct administration is impaired by the nature of the formulation and the polymer (C) is preferably included in the formulation and formulation is preferably carried out in accordance with the process according to the invention.

In a preferred embodiment of the dosage form produced according to the invention, subunits (X) and (Y) are present in multiparticulate form, wherein granules, spheroids, beads or pellets are preferred and the same form, i.e. shape, is selected for both subunit (X) and subunit (Y), such that it is not possible to separate subunits (X) from (Y) by mechanical selection. The multiparticulate forms are preferably of a size in the range from 0.1 to 3 mm, preferably of 0.5 to 2 mm.

The subunits (X) and (Y) in multiparticulate form may also preferably be packaged in a capsule or be press-moulded into a tablet, wherein the final formulation in each case proceeds in such a manner that the subunits (X) and (Y) are also retained in the resultant dosage form.

The multiparticulate subunits (X) and (Y) of identical shape should also not be visually distinguishable from one another so that the abuser cannot separate them from one another by simple sorting. This may, for example, be achieved by the application of identical coatings which, apart from this disguising function, may also incorporate further functions, such as, for example, delayed release of one or more active ingredients or provision of a finish resistant to gastric juices on the particular subunits.

In a further preferred embodiment of the present invention, subunits (X) and (Y) are in each case arranged in layers relative to one another.

The layered subunits (X) and (Y) are preferably arranged for this purpose vertically or horizontally relative to one another in the dosage form produced according to the invention, wherein in each case one or more layered subunits (X) and one or more layered subunits (Y) may be present in the dosage form, such that, apart from the preferred layer sequences (X)-(Y) or (X)-(Y)-(X), any desired other layer sequences may be considered, optionally in combination with layers containing components (a) and/or (b).

Another preferred dosage form produced according to the invention is one in which subunit (Y) forms a core which is completely enclosed by subunit (X), wherein a separation layer (Z) may be present between said layers. Such a structure is preferably also suitable for the above-stated multiparticulate forms, wherein both subunits (X) and (Y) and an optionally present separation layer (Z), which should preferably satisfy the hardness requirement according to the invention, are then formulated in one and the same multiparticulate form using the process according to the invention.

In a further preferred embodiment of the dosage form produced according to the invention, the subunit (X) forms a core, which is enclosed by subunit (Y), wherein the latter comprises at least one channel which leads from the core to the surface of the dosage form.

The dosage form produced according to the invention may comprise, between one layer of the subunit (X) and one layer of the subunit (Y), in each case one or more, preferably one, optionally swellable separation layer (Z) which serves to separate subunit (X) spatially from (Y).

If the dosage form produced according to the invention comprises the layered subunits (X) and (Y) and an optionally present separation layer (Z) in an at least partially vertical or horizontal arrangement, the dosage form preferably takes the form of a tablet, a coextrudate or a laminate, which has been produced using the process according to the invention.

In one particularly preferred embodiment, the entirety of the free surface of subunit (Y) and optionally at least part of the free surface of subunit(s) (X) and optionally at least part of the free surface of the optionally present separation layer(s) (Z) may be coated with at least one barrier layer (Z') which prevents release of component (c) and/or (e) and/or (d) and/or (f). The barrier layer (Z') should preferably also fulfil the hardness conditions according to the invention.

Another particularly preferred embodiment of the dosage form produced according to the invention comprises a vertical or horizontal arrangement of the layers of subunits (X) and (Y) and at least one push layer (p) arranged therebetween, and optionally a separation layer (Z), in which dosage form the entirety of the free surface of the layer structure consisting of subunits (X) and (Y), the push layer and the optionally present separation layer (Z) is provided with a semipermeable coating (E), which is permeable to a release medium, i.e. conventionally a physiological liquid, but substantially impermeable to the active ingredient and to component (c) and/or (d) and/or (f), and wherein this coating (E) comprises at least one opening for release of the active ingredient in the area of subunit (X).

A corresponding dosage form is known to the person skilled in the art, for example under the name oral osmotic therapeutic system (OROS), as are suitable materials and methods for the production thereof, inter alia from U.S. Pat. No. 4,612,008, U.S. Pat. No. 4,765,989 and U.S. Pat. No. 4,783,337. The corresponding descriptions are hereby introduced as a reference and are deemed to be part of the disclosure.

In a further preferred embodiment, the subunit (X) of the dosage form produced according to the invention is in the form of a tablet, the edge face and optionally one of the two main faces of which is covered with a barrier layer (Z') containing component (c) and/or (d) and/or (f).

The person skilled in the art will understand that the auxiliary substances of the subunit(s) (X) or (Y) and of the optionally present separation layer(s) (Z) and/or of the barrier layer(s) (Z') used in the production according to the invention of the respective dosage form will vary as a function of the arrangement thereof in the dosage form, the mode of administration and as a function of the particular active ingredient of the optionally present components (a) and/or (b) and/or (e) and of component (c) and/or (d) and/or (f). The materials which have the requisite properties are in each case known per se to the person skilled in the art.

If release of component (c) and/or (d) and/or (f) from subunit (f) of the dosage form produced according to the invention is prevented with the assistance of a cover, preferably a barrier layer, the subunit may consist of conventional materials known to the person skilled in the art, preferably contain at least one polymer (C) and preferably be produced according to the invention.

If a corresponding barrier layer (Z') is not provided to prevent release of component (c) and/or (d) and/or (f), the materials of the subunits should be selected such that release of the particular component (c) and/or (d) from subunit (Y) is virtually ruled out.

The materials which are stated below to be suitable for production of the barrier layer may preferably be used for this purpose and should preferably contain at least one polymer (C) for fulfilling the hardness conditions.

Preferred materials are those which are selected from the group consisting of alkylcelluloses, hydroxyalkylcelluloses, glucans, scleroglucans, mannans, xanthans, copolymers of poly[bis(p-carboxyphenoxy)propane:sebacic acid], preferably in a molar ratio of 20:80 (marketed under the name Polifeprosan 20®), carboxymethylcelluloses, cellulose ethers, cellulose esters, nitrocelluloses, polymers based on (meth)acrylic acid and the esters thereof, polyamides, polycarbonates, pqlyalkylenes, polyalkylene glycols, polyalkylene oxides, polyalkylene terephthalates, polyvinyl alcohols, polyvinyl ethers, polyvinyl esters, halogenated polyvinyls, polyglycolides, polysiloxanes and polyurethanes and the copolymers thereof.

Particularly suitable materials may be selected from the group consisting of methylcellulose, ethylcellulose, hydroxypropylcellulose, hydroxypropylmethylcellulose, hydroxybutylmethylcellulose, cellulose acetate, cellulose propionate (of low, medium or high molecular weight), cellulose acetate propionate, cellulose acetate butyrate, cellulose acetate phthalate, carboxymethylcellulose, cellulose triacetate, sodium cellulose sulfate, polymethyl methacrylate, polyethyl methacrylate, polybutyl methacrylate, polyisobutyl methacrylate, polyhexyl methacrylate, polyisodecyl methacrylate, polylauryl methacrylate, polyphenyl methacrylate, polymethyl acrylate, polyisopropyl acrylate, polyisobutyl acrylate, polyoctatdecyl acrylate, polyethylene, low density polyethylene, high density polyethylene, polypropylene, polyethylene glycol, polyethylene oxide, polyethylene terephthalate, polyvinyl alcohol, polyvinyl isobutyl ether, polyvinyl acetate and polyvinyl chloride.

Particularly suitable copolymers may be selected from the group comprising copolymers of butyl methacrylate and isobutyl methacrylate, copolymers of methyl vinyl ether and maleic acid of high molecular weight, copolymers of methyl vinyl ether and maleic acid monoethyl ester, copolymers of methyl vinyl ether and maleic anhydride and copolymers of vinyl alcohol and vinyl acetate.

Further materials which are particularly suitable for formulating the barrier layer are starch-filled polycaprolactone (WO98/20073), aliphatic polyesteramides (DE 19 753 534 A1, DE 19 800 698 A1, EP 0 820 698 A1), aliphatic and aromatic polyester urethanes (DE 19822979), polyhydroxyalkanoates, in particular polyhydroxybutyrates, polyhydroxyvalerates, casein (DE 4 309 528), polylactides and copolylactides (EP 0 980 894 A1). The corresponding descriptions are hereby introduced as a reference and are deemed to be part of the disclosure.

The above-stated materials may optionally be blended with further conventional auxiliary substances known to the person skilled in the art, preferably selected from the group consisting of glyceryl monostearate, semi-synthetic triglyceride derivatives, semi-synthetic glycerides, hydrogenated castor oil, glyceryl palmitostearate, glyceryl behenate, polyvinylpyrrolidone, gelatine, magnesium stearate, stearic acid, sodium stearate, talcum, sodium benzoate, boric acid and colloidal silica, fatty acids, substituted triglycerides, glycerides, polyoxyalkylene glycols and the derivatives thereof.

If the dosage form produced according to the invention comprises a separation layer (Z'), said layer, like the uncovered subunit (Y), may preferably consist of the above-stated materials described for the barrier layer. The person skilled in the art will understand that release of the active ingredient or of component (c) and/or (d) from the particular subunit may be controlled by the thickness of the separation layer.

The dosage form produced according to the invention may comprise one or more active ingredients at least partially in delayed-release form, wherein delayed release may be achieved with the assistance of conventional materials and methods known to the person skilled in the art, for example by embedding the active ingredient in a delayed-release matrix or by the application of one or more delayed-release coatings. Active ingredient release must, however, be controlled such that the above-stated conditions are fulfilled in each case, for example that, in the event of correct administration of the dosage form, the active ingredient or active ingredients are virtually completely released before the optionally present component (c) and/or (d) can exert an impairing effect.

Through delayed release, active ingredient release may be so controlled that twice or once daily administration of the dosage form is sufficient, which is advantageous in particular in the case of opioid-containing active ingredients for combatting pain.

Controlled release from the dosage form produced according to the invention is preferably achieved by embedding the active ingredient in a matrix. The auxiliary substances acting as matrix materials control active ingredient release. Matrix materials may, for example, be hydrophilic, gel-forming materials, from which active ingredient release proceeds mainly by diffusion, or hydrophobic materials, from which active ingredient release proceeds mainly by diffusion from the pores in the matrix.

Physiologically acceptable, hydrophobic materials which are known to the person skilled in the art may be used as matrix materials. Polymers, particularly preferably cellulose ethers, cellulose esters and/or acrylic resins are preferably used as hydrophilic matrix materials. Ethylcellulose, hydroxypropylmethylcellulose, hydroxypropylcellulose, hydroxymethylcellulose, poly(meth)acrylic acid and/or the derivatives thereof, such as the salts, amides or esters thereof are very particularly preferably used as matrix materials.

Matrix materials prepared from hydrophobic materials, such as hydrophobic polymers, waxes, fats, long-chain fatty acids, fatty alcohols or corresponding esters or ethers or mixtures thereof are also preferred. Mono- or diglycerides of C12-C30 fatty acids and/or C12-C30 fatty alcohols and/or waxes or mixtures thereof are particularly preferably used as hydrophobic materials.

It is also possible to use mixtures of the abovestated hydrophilic and hydrophobic materials as matrix materials.

Components (C) and the optionally present component (D), may furthermore also optionally serve as additional matrix materials.

If the dosage form produced according to the invention is intended for oral administration, it may also preferably comprise a coating which is resistant to gastric juices and dissolves as a function of the pH value of the release environment. By means of this coating, it is possible to ensure that the dosage form produced according to the invention passes through the stomach undissolved and the active ingredient is only released in the intestines. The coating which is resistant to gastric juices preferably dissolves at a pH value of between 5 and 7.5. The dosage forms produced according to the invention may likewise be provided with delayed-release coatings.

Corresponding materials and methods for the delayed release of active ingredients and for the application of gastric juice-resistant and/or delayed-release coatings are known to the person skilled in the art, for example from "Coated Pharmaceutical Dosage Forms—Fundamentals, Manufacturing Techniques, Biopharmaceutical Aspects, Test Methods and Raw Materials" by Kurt H. Bauer, K Lehmann, Hermann P. Osterwald, Rothgang, Gerhart, 1st edition, 1998, Medpharm Scientific Publishers. The corresponding literature description is hereby introduced as a reference and is deemed to be part of the disclosure.

| List of reference numerals | |
|---|---|
| 1 | Shaft |
| 2 | Direction of flow (extrusion direction) of the product (mixture) |
| 3 | Central spindle |
| 31 | Central spindle flank |
| 4 | Planetary spindle |
| 41 | Planetary spindle flank |
| 42 | Direction of rotation of planetary spindle about own axis |
| 43 | Direction of rotation of planetary spindle about central spindle |
| 5 | Feed screw |
| 6 | Housing (casing) |
| 61 | Housing flank |
| 7 | Apportioning unit |
| 8 | Die |

Method for Determining Breaking Strength

In order to verify whether a polymer may be used as binder with a breaking strength of =500 N, the polymer is press-moulded to form a tablet with a diameter of 10 mm and a height of 5 mm using a force of 150 N at a temperature which at least corresponds to the softening point of the polymer and is determined with the assistance of a DSC diagram of the polymer. Using tablets produced in this manner, breaking strength is determined with the apparatus described below in accordance with the method for determining the breaking strength of tablets published in the European Pharmacopoeia 1997, page 143, 144, method no. 2.9.8. The apparatus used for the measurement is a "Zwick Z 2.5" materials tester, Fmax=2.5 kN, draw max. 1150 mm with the setup comprising 1 column and 1 spindle, clearance behind of 100 mm, a test speed of 0.1800 mm/min and testControl software. Measurement was performed using a pressure piston with screw-in inserts and a cylinder (diam. 10 mm), a force transducer, Fmax. 1 kN, diam.=8 mm, class 0.5 from 10 N, class 1 from 2 N to ISO 7500-1, with manufacturer's test certificate M to DIN 55350-18 (Zwick gross force Fmax=1.45 kN) (all apparatus from Zwick GmbH & Co. KG, Ulm, Germany).

The tablets deemed to be resistant to breaking under a specific load include not only those which have not broken but also those which may have suffered plastic deformation under the action of the force.

The breaking strength of the dosage forms obtained according to the invention may be determined using the same measurement method.

The invention is explained below with reference to Examples. These explanations are given merely by way of example and do not restrict the general concept of the invention.

EXAMPLE 1

| Components | Per tablet | Complete batch |
|---|---|---|
| Tramadol HCl | 150.0 mg | 314 g |
| Polyethylene oxide, NF, MW 7 000 000 (Polyox WSR 303, Dow Chemicals) | 108.8 mg | 228 g |
| Hydroxypropylmethylcellulose (Metholose 90 SH 100 000) | 11.2 mg | 24 g |
| Polyethylene glycol (PEG 6000) | 13.7 mg | 29 g |
| Butylhydroxytoluene | 2.6 mg | 5 g |
| Total weight | 286.3 mg | 600 g |

The components were mixed for 15 minutes in a free-fall mixer before the powder mixture was apportioned into a model BCG 10 planetary-gear extruder with four planetary spindles from LBB Bohle (Ennigerloh, Germany). Apportionment was performed gravimetrically at 3.0 kg per second. The extruder was fitted with an 8 mm diameter extrusion die. Extrusion was performed at a rotational speed of 28.6 rpm with a product temperature of approx. 88° C.

Once the extruded strand had cooled to room temperature, it was cut into disks, the weight of which in each case corresponded to that of the finally formed tablet. The disks were converted into tablets in a model EKO eccentric press from EKO with the assistance of a tabletting tool comprising a round punch with a diameter of 10 mm and a radius of curvature of 8 mm.

The breaking strength of the tablets was determined as stated in the present application. The tablets did not break when exposed to a force of 500 N. The tablets could not be comminuted using a hammer, nor with the assistance of a pestle and mortar.

In vitro release of the active ingredient from the preparation was determined in a paddle stirrer apparatus with sinker in accordance with Pharm. Eur. The temperature of the release medium was 37° C. and the rotational speed of the stirrer 75 min$^{-1}$. The release medium used was intestinal juice, pH 6.8. The quantity of active ingredient released in each case into the dissolution medium at any one time was determined by spectrophotometry.

| Time | Quantity of active ingredient released |
| --- | --- |
| 30 min | 21% |
| 240 min | 86% |
| 480 min | 93% |
| 720 min | 91% |

EXAMPLE 2

| Components | Per tablet | Complete batch |
| --- | --- | --- |
| Tramadol HCl | 100.0 mg | 314 g |
| Polyethylene oxide, NF, MW 7 000 000 (Polyox WSR 303, Dow Chemicals) | 72.5 mg | 228 g |
| Hydroxypropylmethylcellulose (Metholose 90 SH 100 000) | 7.5 mg | 24 g |
| Polyethylene glycol (PEG 6000) | 9.1 mg | 29 g |
| Butylhydroxytoluene | 1.7 mg | 5 g |
| Total weight | 183.3 mg | 600 g |

The components were mixed for 15 minutes in a free-fall mixer before the powder mixture was apportioned into a model BCG 10 planetary-gear extruder with four planetary spindles from LBB Bohle (Ennigerloh, Germany). The extruder was fitted with an extrusion die with 60 bores, each of a diameter of 1 mm. Apportionment was performed gravimetrically at 3 kg per second. Extrusion was performed at a rotational speed of 28.6 rpm with a product temperature of approx. 88° C.

Once the extruded strands had cooled to room temperature, they were cut into cylindrical pellets 1 mm in length, which were packaged in capsules.

The breaking strength of the pellets was determined in accordance with the method stated in the present application. No breakage occurred when a force of 500 N was applied. The tablets could not be comminuted using a hammer, nor with the assistance of a pestle and mortar.

In vitro release of the active ingredient from the preparation was determined in a paddle stirrer apparatus with sinker in accordance with Pharm. Eur. The temperature of the release medium was 37° C. and the rotational speed of the stirrer 75 min$^{-1}$. The release medium used was intestinal juice, pH 6.8. The quantity of active ingredient released in each case into the dissolution medium at any one time was determined by spectrophotometry.

| Time | Quantity of active ingredient released |
| --- | --- |
| 30 min | 58% |
| 60 min | 81% |
| 240 min | 96% |
| 480 min | 99% |

The invention claimed is:

1. A process for the production of an abuse-proofed solid dosage form with a breaking strength of at least 500N, said dosage form comprising at least one opioid active ingredient with potential for abuse and 50-99.9 wt%, relative to the total weight of the dosage form, of polyethylene oxide having a molecular weight of at least one million Daltons, said process comprising heating a mixture comprising the at least one opioid active ingredient with potential for abuse and the polyethylene oxide in a planetary-gear extruder at least until the polyethylene oxide has softened, and thereafter compacting and extruding the mixture with the planetary-gear extruder into formed articles, which are optionally subjected to singulation and shaping to yield a nonmultiparticulate dosage form with a breaking strength of at least 500 N.

2. A process according to claim 1, wherein the active ingredient is selected from the group consisting of oxycodone, morphine, hydromorphone, tramadol and the physiologically acceptable salts thereof.

3. A process according to claim 1, wherein the mixture additionally comprises further auxiliary substances.

4. A process according to claim 1, wherein the planerary-gear extruder has at least three planetary spindles.

5. A process according to claim 1, wherein the planetary-gear extruder has a feed screw and a central spindle with planetary spindles.

6. A process according to claim 1, wherein the formed articles are finally formed and optionally singulated.

7. A process according to claim 1, wherein the formed articles are formed into tablets.

8. A process according to claim 7, wherein the tablets are formed with press molding with the assistance of two counter-rotating rolls with mutually opposing recesses, the construction of which recesses determines the tablet shape.

9. A process according to claim 7, wherein the tablets are in each case formed with the assistance of a die and at least one shaping punch.

10. An abuse-proofed dosage form with a breaking strength of at least 500N obtainable by a process according to claim 1.

11. A process according to claim 2, where the active ingredient is the hydrochloride of oxycodone, morphine, hydromorphine, or tramadol.

12. A process according to claim 3, where the further auxiliary substances are one or more substances selected from the group consisting of waxes (D), antioxidants and plasticizers.

13. A process according to claim 1, where the opioid is in a form selected from the group consisting of physiologically acceptable enantiomers, stereoisomers, diastereomers, racemates and derivatives thereof.

14. A process of claim 13, where the physiologically acceptable derivatives thereof are selected from the group consisting of ethers, esters and amides.

* * * * *